(12) United States Patent
Yamatani et al.

(10) Patent No.: US 8,696,664 B2
(45) Date of Patent: Apr. 15, 2014

(54) BIPOLAR CUTTER

(75) Inventors: Ken Yamatani, Koganei (JP); Shingo Nogami, Machida (JP)

(73) Assignees: Olympus Medical Systems Corp. (JP); Terumo Cardiovascular Systems Corporation, Ann Arbor, MI (US)

( * ) Notice: Subject to any disclaimer, the term of this patent is extended or adjusted under 35 U.S.C. 154(b) by 1072 days.

(21) Appl. No.: 12/032,108

(22) Filed: Feb. 15, 2008

(65) Prior Publication Data

US 2008/0208193 A1 Aug. 28, 2008

Related U.S. Application Data

(63) Continuation of application No. PCT/JP2006/316270, filed on Aug. 18, 2006.

(30) Foreign Application Priority Data

Aug. 18, 2005 (JP) ................................. 2005-237676

(51) Int. Cl.
*A61B 18/14* (2006.01)

(52) U.S. Cl.
USPC ............................................ 606/51; 606/207

(58) Field of Classification Search
USPC ................. 606/48, 51, 52, 206, 207
See application file for complete search history.

(56) References Cited

U.S. PATENT DOCUMENTS

| 5,496,317 | A  | * | 3/1996 | Goble et al. ................. 606/48 |
| 6,019,771 | A  |   | 2/2000 | Bennett et al. |
| 6,110,170 | A  |   | 8/2000 | Taylor et al. |
| 6,228,083 | B1 | * | 5/2001 | Lands et al. ................. 606/50 |
| 6,887,240 | B1 | * | 5/2005 | Lands et al. ................. 606/51 |
| 7,090,673 | B2 | * | 8/2006 | Dycus et al. ................. 606/51 |
| 7,316,683 | B2 | * | 1/2008 | Kasahara et al. ............. 606/45 |
| 7,850,687 | B2 |   | 12/2010 | Kasahara |
| 2003/0065349 | A1 |   | 4/2003 | Hess et al. |
| 2006/0052779 | A1 | * | 3/2006 | Hammill ................. 606/51 |
| 2006/0271042 | A1 | * | 11/2006 | Latterell et al. ............. 606/51 |

FOREIGN PATENT DOCUMENTS

| JP | 2003-199766 | 7/2003 |
| JP | 2005-013332 | 1/2005 |
| WO | WO 02/24089 | 3/2002 |
| WO | WO 2004/052221 | 6/2004 |

OTHER PUBLICATIONS

Extended Search Report by the European Patent Office for European Patent Application No. 06782829.3-2305 issued Feb. 27, 2009.

* cited by examiner

*Primary Examiner* — Michael Peffley
*Assistant Examiner* — Thomas Giuliani
(74) *Attorney, Agent, or Firm* — Ostrolenk Faber LLP

(57) ABSTRACT

A bipolar cutter includes a bipolar cutting treatment portion having a pair of electrodes provided at a front-end portion of an insertion unit inserted in a body of a living thing, a guide portion having a lead passage which captures a living tissue of a cutting target and which leads the living tissue to the treatment portion, the guide portion configured to vary a width of the passage, and a manipulation portion which manipulates the guide portion to vary the passage width. Alternatively, a shape of the lead passage is enlarged from its inner end to its outer end and a lead passage width regulating member being movable between the inner end and the outer end of the lead passage is included. Alternatively, a plurality of lead passages having widths being different from each other is included.

9 Claims, 20 Drawing Sheets

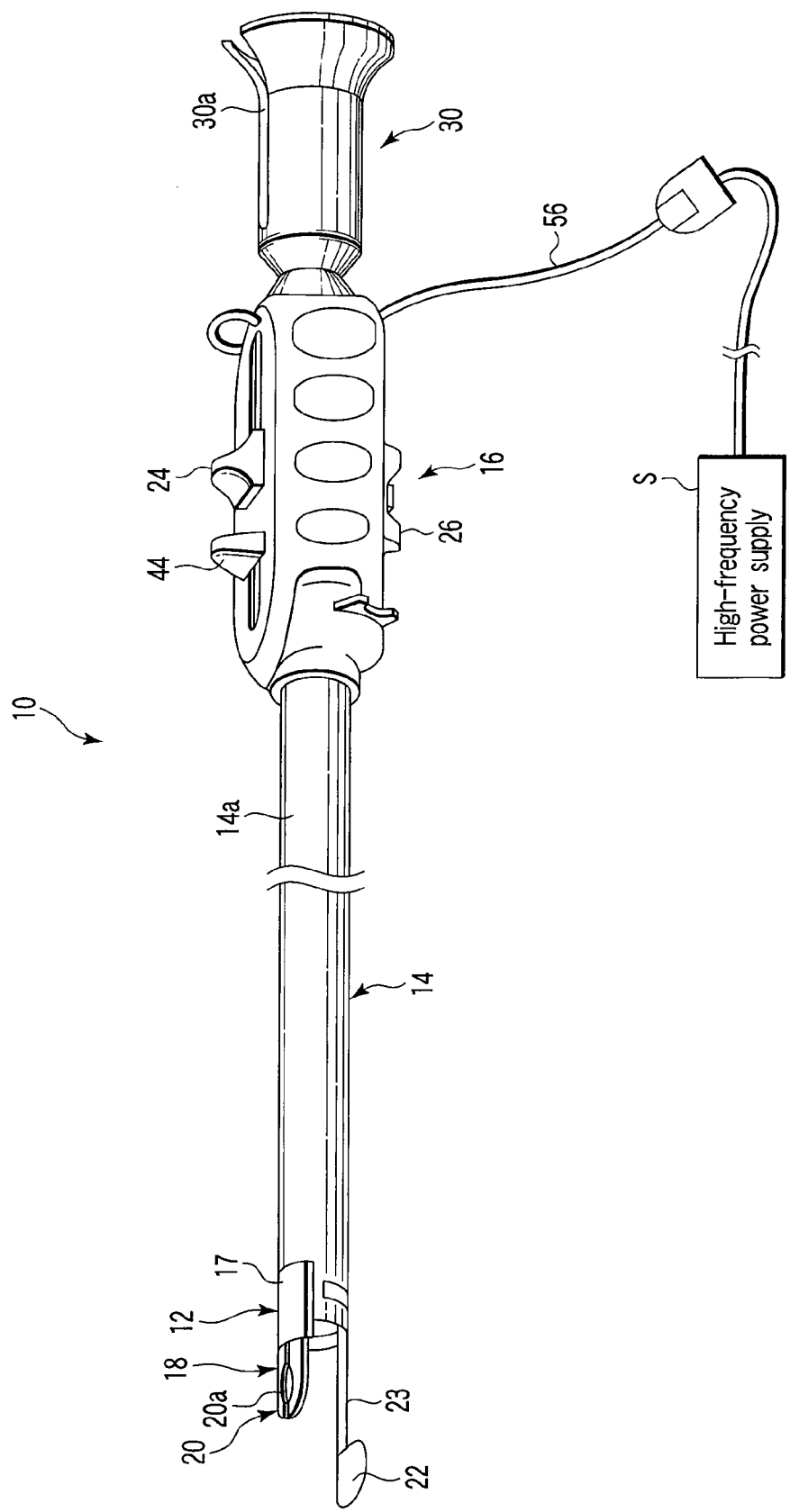
F I G. 1

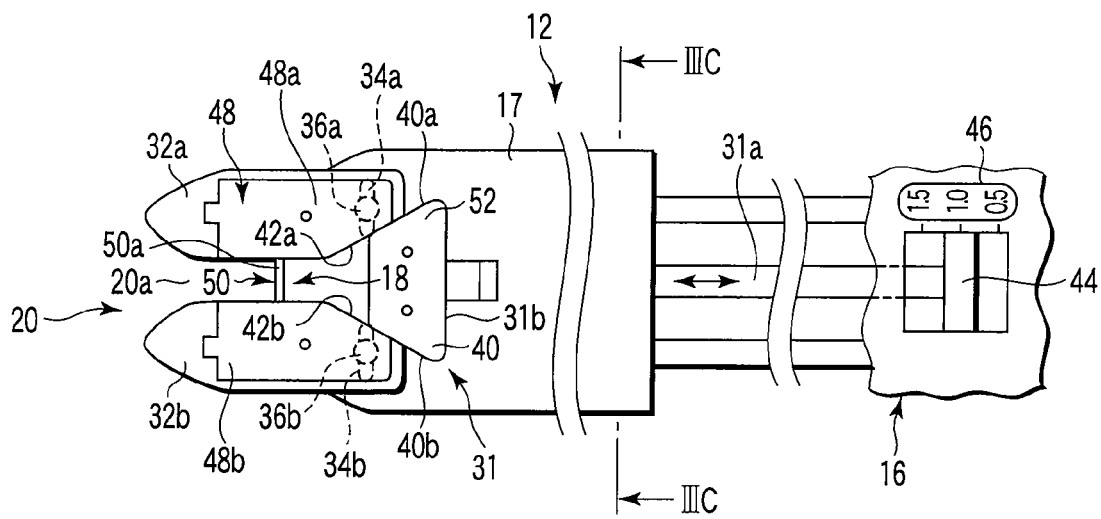
F I G. 3A
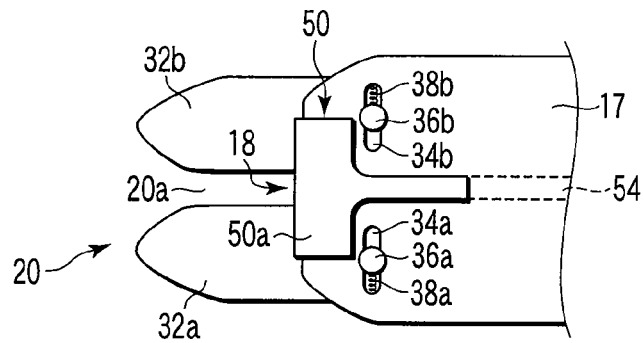
F I G. 3B
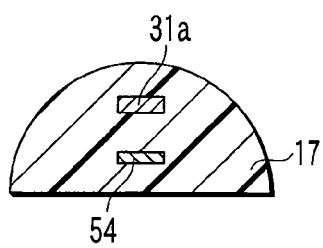
F I G. 3C

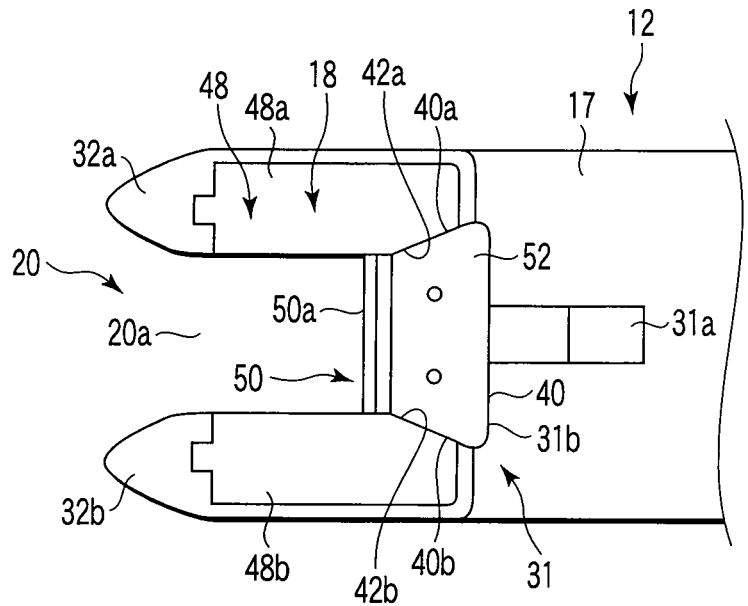
F I G. 8C
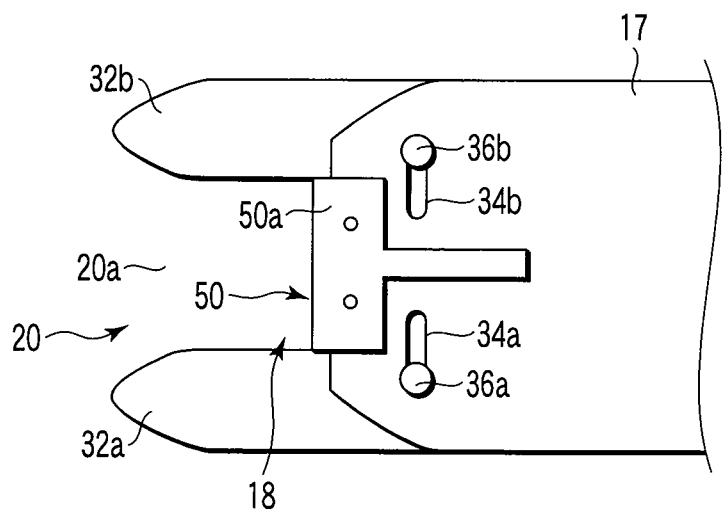
F I G. 8D

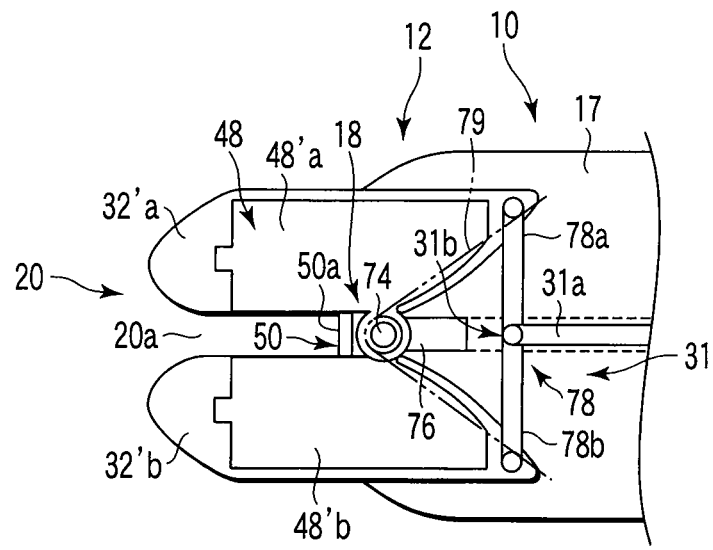
F I G. 9A
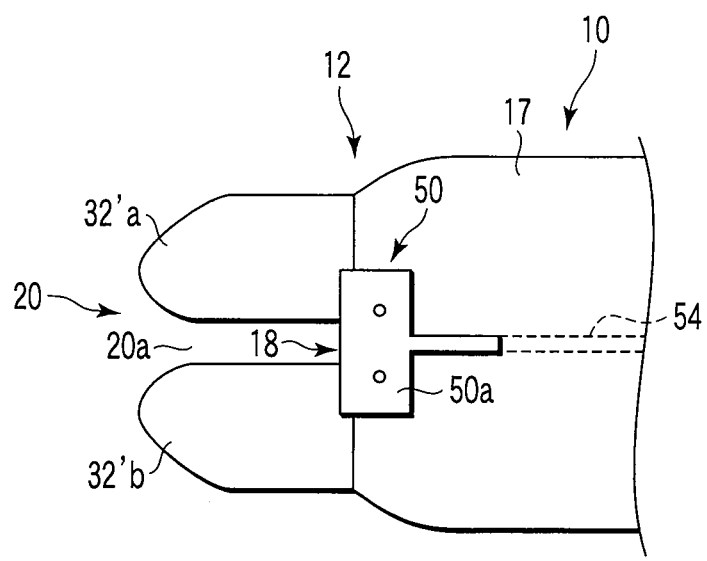
F I G. 9B

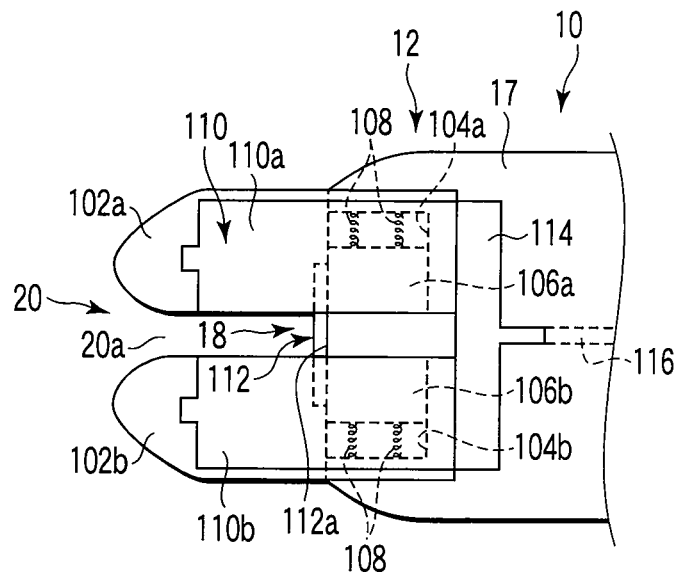
F I G. 11A
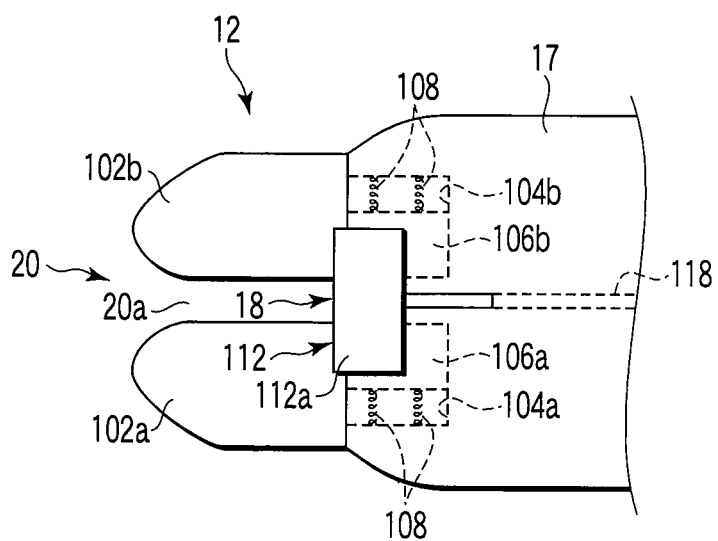
F I G. 11B

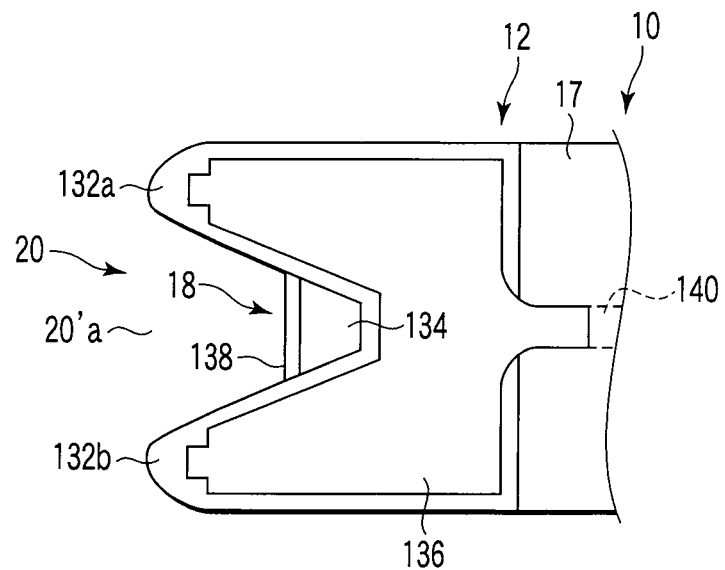
F I G. 13C
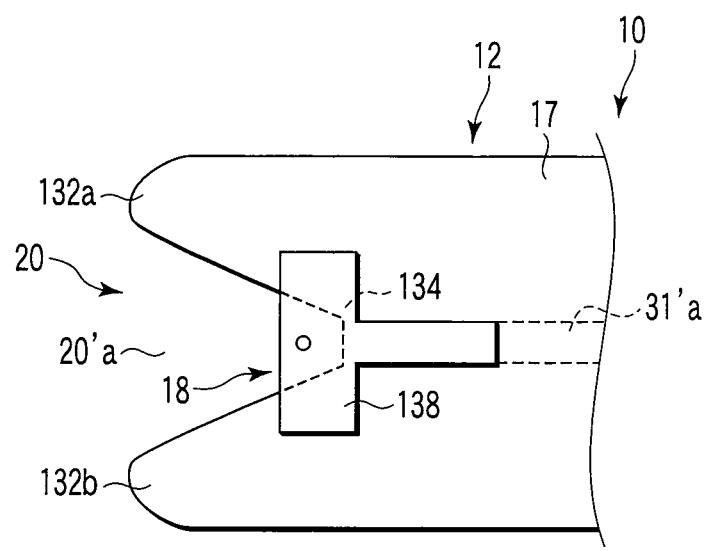
F I G. 13D

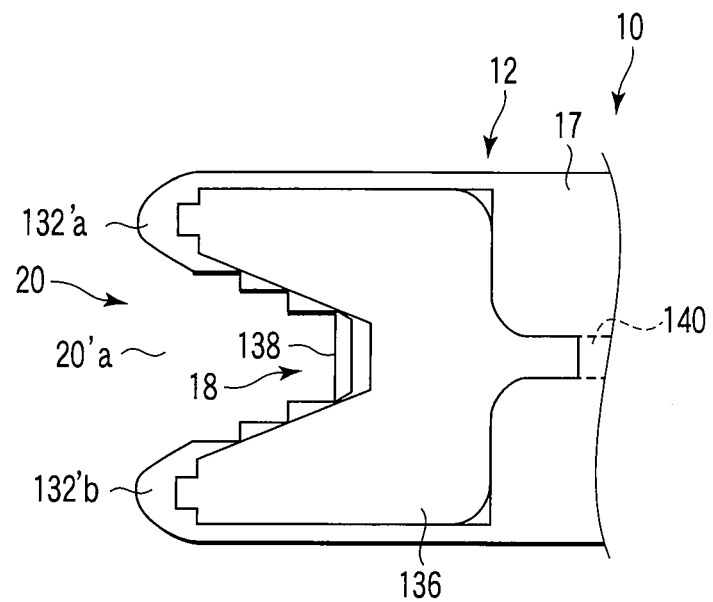
F I G. 15A
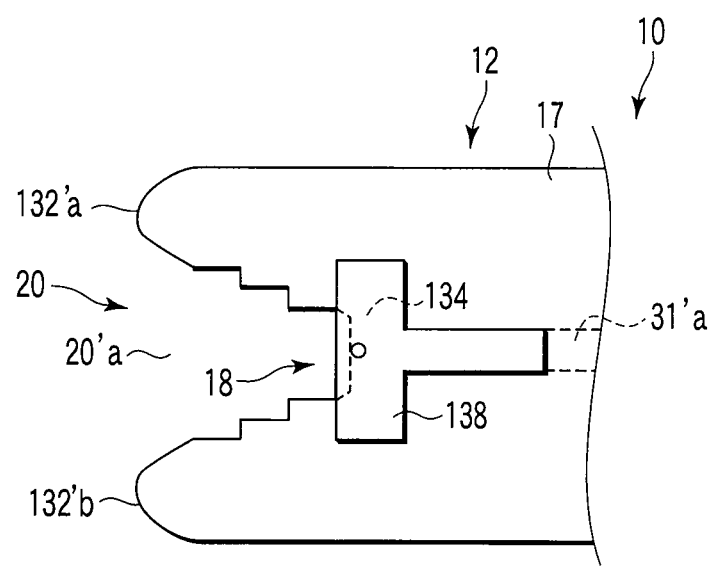
F I G. 15B

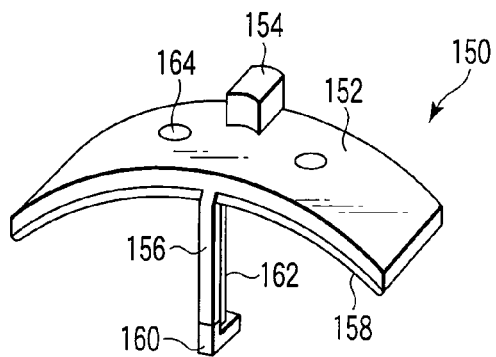
F I G. 16
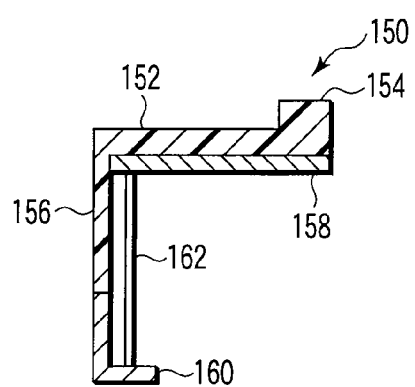
F I G. 17A
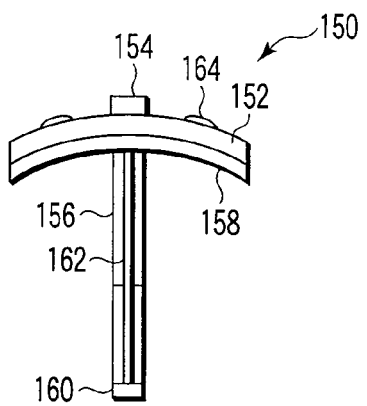
F I G. 17B

BIPOLAR CUTTER

CROSS REFERENCE TO RELATED APPLICATIONS

This is a Continuation Application of PCT Application No. PCT/JP2006/316270, filed Aug. 18, 2006, which was published under PCT Article 21(2) in Japanese.

This application is based upon and claims the benefit of priority from prior Japanese Patent Application No. 2005-237676, filed Aug. 18, 2005, the entire contents of which are incorporated herein by reference.

BACKGROUND OF THE INVENTION

1. Field of the Invention

The present invention relates to a bipolar cutter which is inserted into a body of a living thing and which cuts a living tissue as a cutting target in the living body and cauterizes a cutting section of the living tissue by using a pair of electrodes.

2. Description of the Related Art

Conventionally, there is known a bipolar cutter including a pair of jaws which can open and close and which is electrically conductive. After being inserted into the body of the living thing, the pair of jaws is opened to nip the living tissue as the cutting target in the body of the living thing therebetween. Then, the pair of jaws is closed while an electric current is applied thereto, whereby the living tissue nipped by the jaws is cut and its cut surface is cauterized.

Conventionally, there is also known a bipolar cutter including a pair of electrodes which are separated from each other with a predetermined distance and a cutting tool. The pair of electrodes is inserted into a body of a living thing and nips a living tissue as a cutting target in the body of the living thing therebetween. Then, while an electric current is applied to the pair of electrodes, the living tissue nipped between the electrodes is cut by using the cutting tool, whereby a cut surface of the living tissue is cauterized.

In these conventional bipolar cutters, the living tissue as the cutting target cannot be cut by simply applying an electric current to the pair of jaws or the pair of electrodes while the jaws or electrodes are nipping the living tissue as the cutting target. In order to cut the living tissue as the cutting target, a closing operation of the pair of jaws or an operation of the cutting tool is required.

Jpn. Pat. Appln. KOKAI Publication No. 2003-199766 discloses a bipolar cutter, in which a V-shaped notch is formed in a front-end portion of an insertion unit introduced in a body of a living thing and a pair of electrodes is disposed at an inner end of the V-shaped notch. One of contact areas of the pair of electrodes exposed at the inner end is set smaller than the other contact area. In the conventional bipolar cutter disclosed in Jpn. Pat. Appln. KOKAI Publication No. 2003-199766, the inner end of the notch of the insertion unit introduced in the living body is pressed against a living tissue of a cutting target in the living body, whereby the living tissue is cut by one electrode having the smaller contact area and at the same time a living tissue around the cut surface is cauterized by the other electrode having the larger contact area.

In the conventional bipolar cutter described in the above described Publication, only a living tissue having a size within a range of the V-shaped notch size can be cut because the size of the V-shaped notch is fixed.

BRIEF SUMMARY OF THE INVENTION

According to one aspect of this invention, a bipolar cutter comprises: an insertion unit inserted in a body of a living thing; a bipolar cutting treatment portion having a pair of electrodes provided at a front-end portion of the insertion unit; a guide portion provided in the front-end portion of the insertion unit and having a lead passage which captures a living tissue of a cutting target in the body of the living thing and which leads the living tissue to the bipolar cutting treatment portion, the guide portion being configured to vary a width of the lead passage; and a lead passage width variable manipulation portion which manipulates the guide portion to vary the width of the lead passage.

According to another aspect of this invention, a bipolar cutter comprises: an insertion unit inserted in a body of a living thing; a bipolar cutting treatment portion having a pair of electrodes provided in a front-end portion of the insertion unit; and a guide portion provided in the front-end portion of the insertion unit and having a lead passage which captures a living tissue of a cutting target in the body of the living thing and which leads the living tissue to the bipolar cutting treatment portion, a width of the lead passage of the guide portion being enlarged as the lead passage being away from the front-end portion of the insertion unit, the guide portion further comprising a lead passage width regulating member which is movable along a lengthwise center line of the insertion unit between an inner end of the lead passage and a position close to an outer end of the lead passage, wherein one of the pair of electrodes of the bipolar cutting treatment portion is disposed at a part of the guide portion which is along the lead passage, and the other of the pair of electrodes is disposed in a part of the lead passage width regulating member which is orientated toward an outer end of the lead passage.

According to further aspect of this invention, a bipolar cutter comprises: an insertion unit inserted in a body of a living thing; a bipolar cutting treatment portion having a pair of electrodes provided in a front-end portion of the insertion unit; and a guide portion provided in the front-end portion of the insertion unit and having a lead passage which captures a living tissue of a cutting target in the body of the living thing and which leads the living tissue to the bipolar cutting treatment portion, the guide portion including a plurality of lead passages having widths being different from each other.

According to more further aspect of this invention, a bipolar cutter comprises: an insertion unit inserted in a body of a living thing; a bipolar cutting treatment portion having a pair of electrodes provided in a front-end portion of the insertion unit; and a guide portion provided in the front-end portion of the insertion unit and having a lead passage which captures a living tissue of a cutting target in the body of the living thing and which leads the living tissue to the bipolar cutting treatment portion, the guide portion further having a pair of capturing members which forms the lead passage therebetween, at least one of the pair of capturing members being movably provided in the front-end portion of the insertion unit and varying a width of the lead passage, and the at least one of the pair of capturing members being urged in a direction in which the width of the lead passage is decreased.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic perspective view of a blood vessel harvesting apparatus (harvester) according to a first embodiment of a bipolar cutter of the present invention and used in combination with an endoscope.

FIG. 3A is a schematic plan view of a cutter main unit of the blood vessel harvesting apparatus (harvester) shown in FIG. 1.

FIG. 3B is a bottom view of the cutter main unit shown in FIG. 3A.

FIG. 3C is a schematic transverse sectional view taken along a line IIIC-IIIC of FIG. 3A.

FIG. 8C is a schematic plan view showing the cutter main unit shown in FIG. 3A in a state in which the pair of capturing members A is kept farthest away from each other.

FIG. 8D is a schematic bottom view of the cutter main unit shown in FIG. 8C.

FIG. 9A is a schematic plan view showing a cutter main unit of a blood vessel harvesting apparatus (harvester) according to a second embodiment of the bipolar cutter of the invention in a state in which a pair of capturing members is brought closest to each other.

FIG. 9B is a schematic bottom view of the cutter main unit shown in FIG. 9A.

FIG. 11A is a schematic plan view showing a cutter main unit of a blood vessel harvesting apparatus (harvester) according to a fourth embodiment of the bipolar cutter of the present invention in a state in which a pair of capturing members is brought closest to each other.

FIG. 11B is a schematic bottom view of the cutter main unit shown in FIG. 11A.

FIG. 13C is a schematic plan view showing the cutter main unit shown in FIG. 13A in a state in which the lead passage width regulating member is kept farthest away from the inner end of the lead passage.

FIG. 13D is a schematic bottom view of the cutter main unit shown in FIG. 13C.

FIG. 15A is a schematic plan view of a modification of the cutter main unit shown in FIG. 13A.

FIG. 15B is a schematic bottom view of the modification of the cutter main unit shown in FIG. 15A.

FIG. 16 is a schematic perspective view of an output checking device for the bipolar cutter of the present invention.

FIG. 17A is a schematic longitudinal sectional view of the output checking device shown in FIG. 16.

FIG. 17B is a schematic front view of the output checking device shown in FIG. 16.

DETAILED DESCRIPTION OF THE INVENTION

[First Embodiment]

A blood vessel harvesting apparatus (harvester) 10 which is according to a first embodiment of the bipolar cutter of the invention and which is used in combination with an endoscope will be described with reference to FIGS. 1 to 8D.

Figure 2:
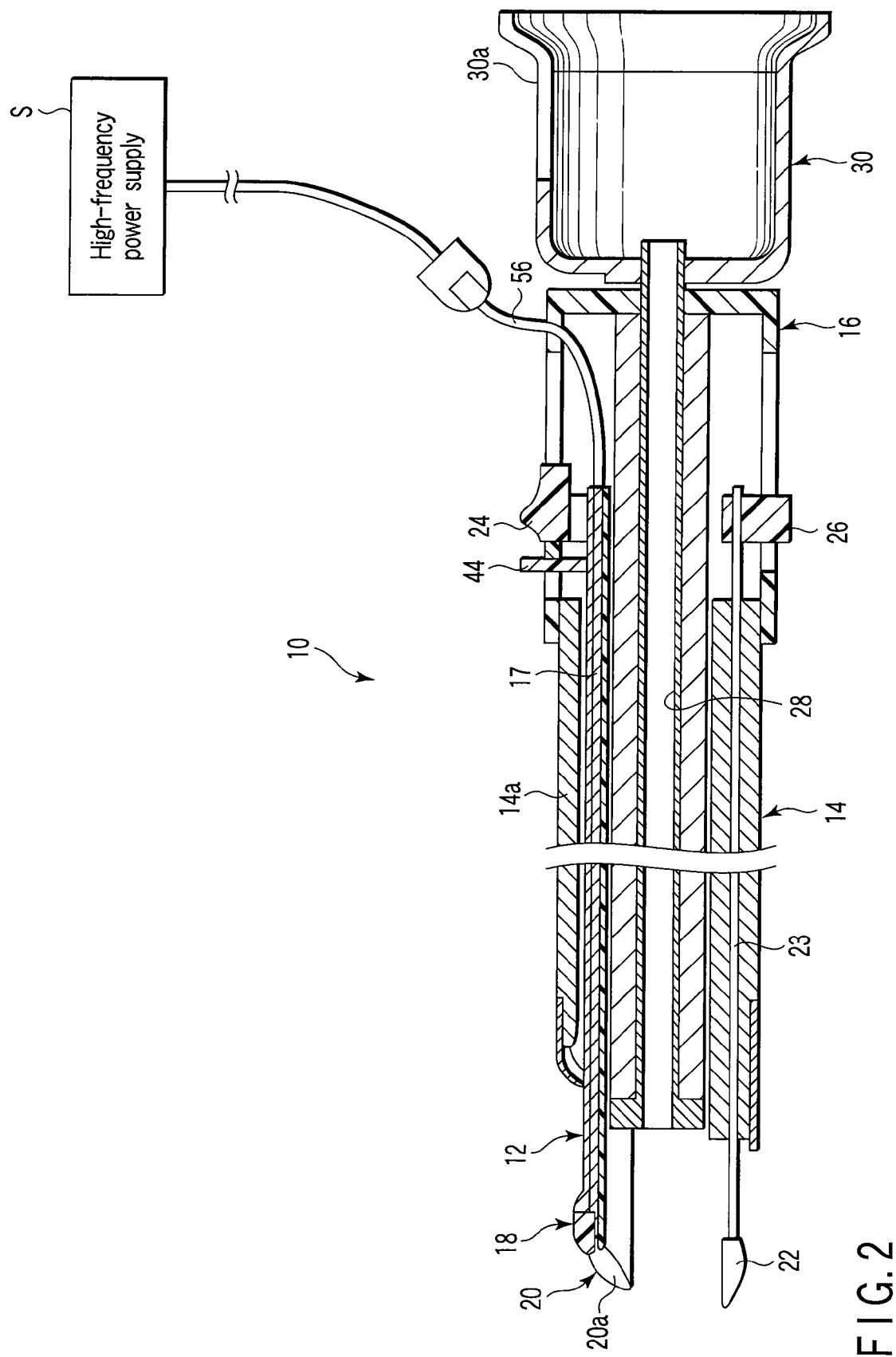
FIG. 2 is a schematic longitudinal sectional view of the blood vessel harvesting apparatus (harvester) shown in FIG. 1.

FIG. 1 shows a schematic perspective view of the blood vessel harvesting apparatus (harvester) 10 which is according to the first embodiment of the bipolar cutter of the invention and which is used in combination with the endoscope. And, FIG. 2 shows a schematic longitudinal sectional view of the blood vessel harvesting apparatus (harvester) 10 shown in FIG. 1.

The blood vessel harvesting apparatus (harvester) 10 comprises an insertion unit 14 which supports a cutter main unit 12 and which includes a metal sheath 14a to be inserted in a body of a living thing (in this case, a human body), and a grip unit 16 which is coupled to a base-end portion of the sheath 14a to be disposed in an outside of the body of the living thing and which is made of a nonconductive material.

The cutter main unit 12 includes a movable support body 17 which extends through the sheath 14a in a lengthwise direction of the sheath 14a and which is moveable in the lengthwise direction of the sheath 14a with respect to the sheath 14a. The movable support body 17 is made of a nonconductive material, and includes a front-end portion located in a front-end portion of the sheath 14a and a base-end portion located in the grip portion 16.

The cutter main unit 12 also includes a bipolar cutting treatment portion 18 which is provided in the front-end portion of the movable support body 17, which cuts a living tissue (in this case, a blood vessel) of a cutting target in the body of the living thing, and which cauterizes a cut surface of the living tissue.

The cutter main unit 12 further includes a guide portion 20 which is provided in the front-end portion of the movable support body 17 and which includes a lead passage 20a. The lead passage 20a captures the living tissue (in this case, the blood vessel) of the cutting target in the body of the living thing and leads the living tissue (in this case, the blood vessel) to the bipolar cutting treatment portion 18. The guide portion 20 is configured to be able to vary a width of the lead passage 20a.

In the front-end portion of the sheath 14a, a blood vessel retainer 22 is further disposed at a position where the blood vessel retainer 22 faces the guide portion 20 of the cutter main unit 12 in a radial direction of the front-end portion. The blood vessel retainer 22 is fixed to one end portion of a retainer manipulating member 23 projecting from the front-end portion of the sheath 14a. The retainer manipulating member 23 extends in the sheath 14a in the lengthwise direction of the sheath 14a from the front-end portion of the sheath 14a to the grip unit 16, and is movable in the lengthwise direction of the sheath 14a with respect to the sheath 14a.

In the grip unit 16, a cutter manipulation slider 24 and a retainer manipulating slider 26 are supported to be movable in the lengthwise direction of the sheath 14a.

The cutter manipulation slider 24 is coupled to the base-end portion of the movable support body 17. By moving the cutter manipulation slider 24 within a predetermined range in the lengthwise direction with respect to the grip unit 16, the front-end portion (i.e., the bipolar cutting treatment portion 18 and the guide portion 20) of the movable support body 17 can be moved to close to or far away from the front-end portion of the sheath 14a in the lengthwise direction.

Further, the retainer manipulating slider 26 is coupled to the other end portion of the retainer manipulating member 23 disposed in the grip unit 16. By moving the retainer manipulating slider 26 within a predetermined range in the lengthwise direction with respect to the grip unit 16, a front-end portion (i.e., the blood vessel retainer 22) of the retainer manipulating slider 26 can be moved to close to or far away from the front-end portion of the sheath 14a in the lengthwise direction.

In a center of the radial direction of the sheath 14a, a metal endoscope insertion pipe 28 is disposed and extends in the lengthwise direction of the sheath 14a from the front-end portion of the sheath 14a to the grip unit 16. A base-end portion of the endoscope insertion pipe 28 in the grip unit 16 projects outward from a base-end portion of the grip unit 16 and a tubular endoscope holder 30 is fixed to the base-end portion of the endoscope insertion pipe 28.

An escape opening 30a is formed in a circumferential wall of the endoscope holder 30. When an insertion unit of an endoscope (not shown) is inserted in the endoscope insertion pipe 28, a manipulation unit of the endoscope is fitted in the endoscope holder 30 while a light guide connector of the endoscope is introduced into the escape opening 30a, so that the manipulation unit is stably retained.

Next, a configuration of the cutter main unit 12 of the blood vessel harvesting apparatus (harvester) 10 according to this embodiment will be described in detail with reference to FIGS. 3A to 3C.

FIG. 3A is a schematic plan view of the cutter main unit 12 shown in FIG. 1, FIG. 3B is a bottom view of the cutter main unit 12 shown in FIG. 3A, and FIG. 3C is a schematic transverse sectional view taken along a line IIIC-IIIC in FIG. 3A.

In FIG. 3A, a lead passage width variable manipulation portion 31 which manipulates the guide portion 20 in the front-end portion of the movable support body 17 and which varies the width of the lead passage 20a is shown. A detailed configuration of the lead passage width variable manipulation portion 31 will be described later.

As shown in FIG. 3A, the guide portion 20 in the front-end portion of the movable support body 17 includes a pair of capturing members 32a, 32b which projects outwardly from the front-end portion in parallel to each other along the lengthwise direction of the movable support body 17. The pair of capturing members 32a, 32b forms the lead passage 20a therebetween. Each of the pair of capturing members 32a, 32b is made of a nonconductive material and its projected end portion is dully pointed. As a result, in the lead passage 20a, an outer-end portion corresponding to projected end portions of the capturing members 32a and 32b is gradually broadened toward the outer end.

At least one of the capturing members 32a, 32b (in this embodiment, both the capturing members 32a, 32b) is movably provided in the front-end portion of the movable support body 17 so as to vary the width of the lead passage 20a.

The lead passage width variable manipulation portion 31 includes a lengthwise moving member 31a which is movable along the lengthwise direction of the movable support body 17 and a capturing member driving mechanism 31b which drives the at least one of the capturing members 32a, 32b (in this embodiment, both the capturing members 32a, 32b) so as to vary the width of the lead passage 20a in accordance with the movement of the lengthwise moving member 31a.

The at least one of the capturing members 32a, 32b (in this embodiment, both the capturing members 32a, 32b) is provided to move in a direction intersecting a lengthwise center line of the movable support body 17 (in this embodiment, a direction orthogonal to the lengthwise center line of the movable support body 17) in parallel with the lengthwise center line with respect to the front-end portion of the movable support body 17, and is urged in a direction in which the width of the lead passage 20a formed between the capturing members 32a, 32b is decreased.

Moving and urging the pair of capturing members 32a, 32b with respect to the front-end portion of the movable support body 17 can be achieved by a well-known configuration.

For example, an end face of each base-end portion of the pair of capturing members 32a, 32b is extended in the direction intersecting the lengthwise center line of the movable support body 17 (in this embodiment, the direction orthogonal to the lengthwise center line of the movable support body 17), and a stepped portion having a guide surface extended in the direction intersecting the lengthwise center line (in this embodiment, the direction orthogonal to the lengthwise center line) is formed in the front-end portion of the movable support body 17. By abutting the end face of each base-end portion of the pair of capturing members 32a, 32b against the guide surface of the front-end portion of the movable support body 17 and by sliding it thereon, the pair of capturing members 32a, 32b can be moved in the above-described manner with respect to the front-end portion of the movable support body 17.

In a pair of regions in the front-end portion of the movable support body 17, these regions corresponding to the base-end portions of the pair of capturing members 32a, 32b, a pair of guide slots 34a, 34b which extends in the direction intersecting the lengthwise center line of the movable support body 17 (in this embodiment, the direction orthogonal to the lengthwise center line) is formed. A pair of guide pins 36a, 36b which is inserted in the pair of guide slots 34a, 34b in the pair of regions of the front-end portion of the movable support body 17 is fixed to the base-end portions of the capturing members 32a, 32b. A pair of urging members 38a, 38b such as compression coil springs is disposed in the pair of guide slots 34a, 34b in the pair of regions of the front-end portion of the movable support body 17. The pair of urging members 38a, 38b urges the pair of guide pins 36a, 36b inserted in the pair of guide slots 34a, 34b to close the pair of guide pins 36a, 36b to the lengthwise center line of the movable support body 17. This means that the pair of urging members 38a, 38b urges the pair of capturing members 32a, 32b so as to decrease the width of the lead passage 20a formed between the capturing members 32a, 32b.

The lengthwise moving member 31a of the lead passage width variable manipulation portion 31 has one end portion located in the front-end portion of the movable support body 17 and the other end portion located in the grip unit 16. The capturing member driving mechanism 31b of the lead passage width variable manipulation portion 31 includes a cam member 40 interposed between the one end portion of the lengthwise moving member 31a and the at least one of the capturing members 32a, 32b (in this embodiment, both the capturing members 32a, 32b).

The cam member 40 includes at least one of a pair of cam surfaces 40a, 40b (in this embodiment, both the cam surfaces 40a, 40b). The at least one of the cam surfaces 40a, 40b (in this embodiment, both the cam surfaces 40a, 40b) contacts the at least one of the capturing members 32a, 32b (in this embodiment, both the capturing members 32a, 32b), and moves the at least one of the capturing members 32a, 32b (in this embodiment, both the capturing members 32a and 32b) by the urging force or against the urging force in accordance with the movement of the lengthwise moving member 31a in the lengthwise direction of the movable support body 17.

Particularly, edges facing each other in the base-end portions of the capturing members 32a, 32b are formed as cam sliding/contacting edges 42a, 42b which are inclined so as to be gradually separated from each other toward the end face of the base-end portion. The cam member 40 is disposed between the cam sliding/contacting edges 42a, 42b of the base-end portions of the capturing members 32a, 32b, and is fixed to the one end portion of the lengthwise moving member 31a. The cam surfaces 40a, 40b of the cam member 40 are inclined in accordance with the cam sliding/contacting edges 42a, 42b of the base-end portions of the pair of capturing members 32a, 32b, and the cam surfaces 40a, 40b contact the cam sliding/contacting edges 42a, 42b, respectively.

The other end portion of the lengthwise moving member 31a, located in the grip unit 16, is coupled to a lead passage width variable slider 44 which projects toward the outside space from the grip unit 16 and which is supported by the grip unit 16 to be movable in the lengthwise direction of the sheath 14a. A lead passage width index 46 is disposed at a position on an outer surface of the grip unit 16, the position being adjacent to the lead passage width variable slider 44. The lead passage width index 46 displays the width of the lead passage 20a formed between the capturing members 32a, 32b in accordance with the position of the lead passage width variable slider 44.

Next, a configuration of the bipolar cutting treatment portion 18 provided in the front-end portion of the movable support body 17 will be described below.

The bipolar cutting treatment portion 18 has a pair of electrodes, i.e., an application electrode 48 and a return electrode 50, which are provided in the front-end portion of the movable support body 17.

The application electrode 48 includes a pair of conductive terminal members 48a, 48b fixed to the pair of capturing members 32a, 32b. In the pair of capturing members 32a, 32b, the pair of conductive terminal members 48a, 48b covers a pair of facing edges forming the lead passage 20a between the capturing members 32a, 32b and the pair of cam sliding/contacting edges 42a and 42b.

The return electrode 50 includes a conductive terminal member 50a fixed to the front-end portion of the movable support body 17. The conductive terminal member 50a covers a region of the front end of the front-end portion of the movable support body 17, the region having a size being larger than the maximum width of the lead passage 20a formed between the capturing members 32a and 32b. This means that the conductive terminal member 50a is disposed at an inner end of the lead passage 20a.

An intermediate conductive terminal member 52 is fixed to the cam member 40, and the intermediate conductive terminal member 52 covers the pair of cam surfaces 40a, 40b. Accordingly, the intermediate conductive terminal member 52 is electrically connected to the pair of conductive terminal members 48a, 48b of the application electrode 48. The intermediate conductive terminal member 52 is further electrically connected to one end portion of a first lead wire (not shown) extending in the lengthwise direction of the lengthwise moving member 31a in the lengthwise moving member 31a. The other end portion of the first lead wire (not shown) is exposed at the other end portion of the lengthwise moving member 31a disposed in the grip unit 16.

By making the lengthwise moving member 31a of a conductive material, it can perform the function of the first lead wire (not shown). In the case, the lead passage variable manipulation slider 44 is made of a nonconductive material.

The conductive terminal member 50a of the return electrode 50 is electrically connected to one end portion of a second lead wire 54 extending in the lengthwise direction of the movable support body 17 in the movable support body 17. The other end portion of the second lead wire 54 is exposed on the other end portion of the lengthwise moving member 31a disposed in the grip unit 16.

In the grip unit 16, one end portion of a high-frequency power supply connection cable 56 is electrically connected to the other end portion of the first lead wire (not shown), exposed on the other end portion of the lengthwise moving member 31a, for the pair of conductive terminal members 48a, 48b of the application electrode 48, and is also electrically connected to the other end portion of the second lead wire 54, exposed on the other end portion of the movable support body 17, for the return electrode 50.

The high-frequency power supply connection cable 56 extends toward the outside of the grip unit 16, and a high-frequency power supply S is detachably connected to the extended end portion, i.e., the other end portion, of the high-frequency power supply connection cable 56.

An example of an operation method for partially harvesting a blood vessel from the inside of the body of the living thing by using the blood vessel harvesting apparatus (harvester) 10 will be described with reference to FIGS. 4 to 8D. In this example, a large saphenous vein 62 is harvested from the inside of a leg 60 of a human body.

Figure 4:
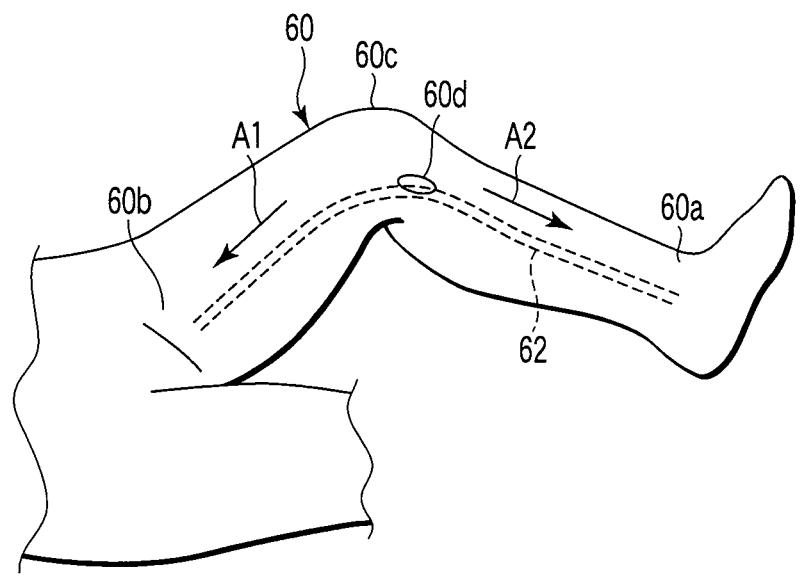
FIG. 4 is a schematic view for explaining a first stage of an example of an operation method by which a part of a large saphenous vein of a human leg is harvested by the blood vessel harvesting apparatus (harvester) shown in FIG. 1.

As shown in FIG. 4, the large saphenous vein 62 is extended between an ankle 60a and an inguinal region 60b near the cuticle in the leg 60 of the human body.

In a first stage of the example of the operation method, an operator cuts a portion of the leg 60 corresponding to the large saphenous vein 62 immediately below a backside of a knee 60c by a surgical knife, and forms an opening 60d having a length of about 2.5 cm. Then, a part of the large saphenous vein 62 corresponding to the opening 60d is separated from the living tissue around the large saphenous vein 62 and is exposed in the opening 60d.

Figure 5:
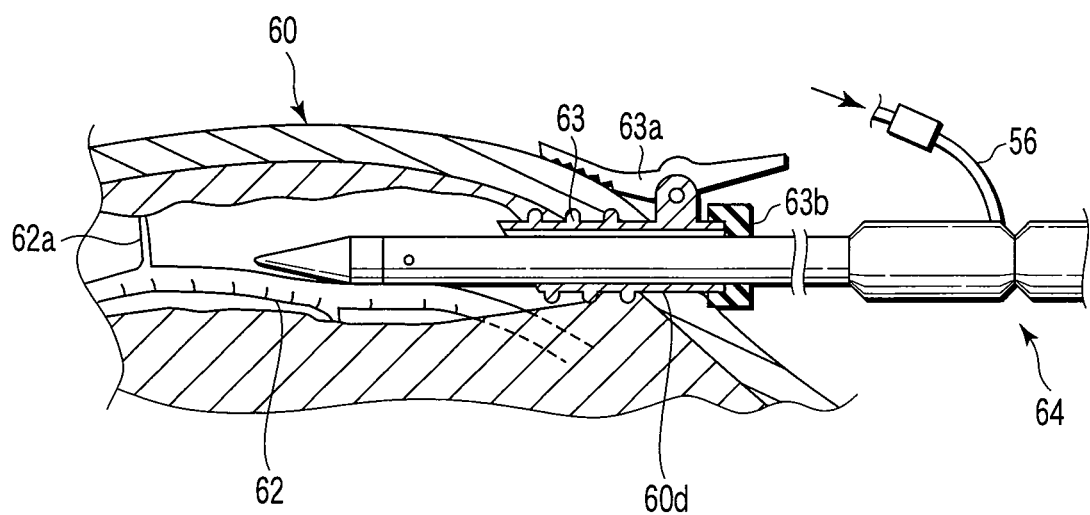
FIG. 5 is a sectional view schematically showing a state in which the large saphenous vein is separated from a living tissue located around the large saphenous vein in an inside of the leg by using a peeling forceps inserted along an endoscope in a trocar put into an opening of the leg shown in FIG. 4 in the first stage of the example of the operation method.

After a trocar 63 is inserted in the opening 60d, the trocar 63 is left in the opening 60d as shown in FIG. 5. The trocar 63 is tentatively fixed to the opening 60d by an openable clip 63a.

Initially, the inner end of the trocar 63 is orientated toward the inguinal region 60b as shown by an arrow A1 of FIG. 4, and a blood vessel peeling device (dissector) 64 together with the endoscope (not shown) is inserted into a hole of the trocar 63 through a sealing member 63b located at an outer end of the trocar 63. Then, the operator moves the dissector 64 along the large saphenous vein 62 from the opening 60d to the inguinal region 60b of the leg 60 while viewing an endoscope image, and separates a part of the large saphenous vein 62 located in a range from the opening 60d to the inguinal region 60b from the living tissues surrounding the part by using the dissector 64.

Then, the endoscope and the dissector 64 are tentatively drawn from the hole of the trocar 63, and the inner end of the trocar 63 is orientated toward the ankle 60a as shown by an arrow A2 of FIG. 4. The dissector 64 together with the endoscope (not shown) is inserted again into the hole of the trocar 63 through the sealing member 63b located at the outer end of the trocar 63. Then, the operator moves the dissector 64 along the large saphenous vein 62 from the opening 60d to the ankle 60a in the leg 60 while viewing the endoscope image, and separates a part of the large saphenous vein 62 located in a range from the opening 60d to the ankle 60a from the surrounding tissues surrounding the part by using the dissector 64.

At the end of the first stage of the example of the above operation method, the endoscope and the dissector 64 are drawn from the hole of the trocar 63.

After the first stage of the example of the operation method is finished, the large saphenous vein 62 separated from the surrounding tissues in the range of the inguinal region 60b to the ankle 60a in the leg 60 is connected to the surrounding living tissue only by plural collateral veins 62a.

Figure 6:
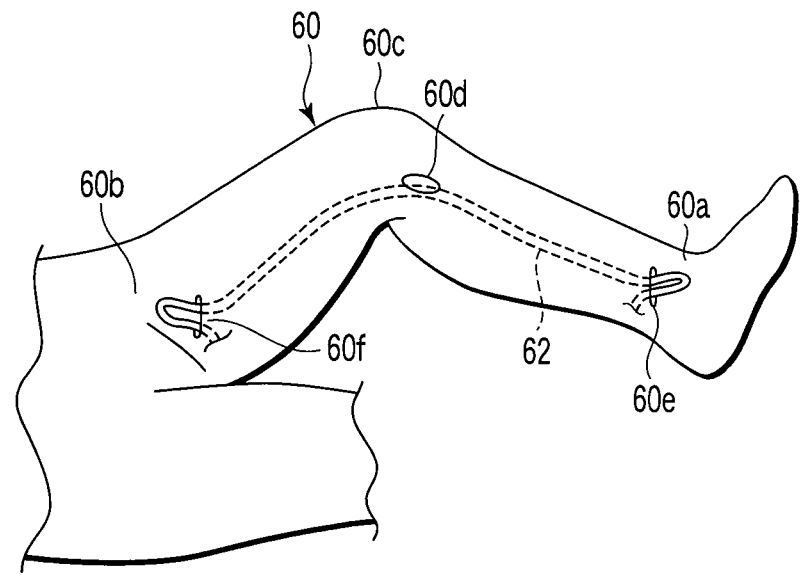
FIG. 6 is a schematic view for explaining a second stage of the example of the operation method.

In a second stage of the example of the operation method, as shown in FIG. 6, the operator cuts portions corresponding to both end portions of the large saphenous vein 62 located at the ankle 60a and the inguinal region 60b in the leg 60 by using the surgical knife, and forms openings 60e, 60f. Both end portions of the large saphenous vein 62 are drawn from the openings 60e, 60f and tied with strings respectively.

Figure 7:
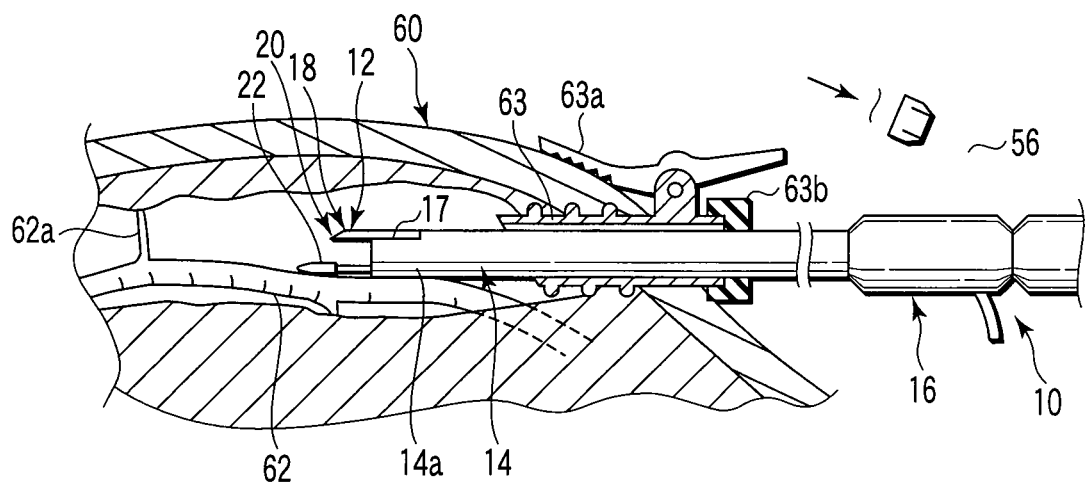
FIG. 7 is a sectional view schematically showing a state in which, instead of the peeling forceps shown in FIG. 5, the blood vessel harvesting apparatus (harvester) according to the first embodiment of the bipolar cutter of the present invention is inserted in the trocar shown in FIG. 5 to harvest the large saphenous vein, in a third stage of the example of the operation method.

As shown in FIG. 7, in a third stage of the example of the operation method, the operator orientates the inner end of the trocar 63 toward the inguinal region 60b as shown by the arrow A1 of FIG. 4, and inserts the insertion unit 14 of the blood vessel harvesting apparatus (harvester) 10 shown in FIGS. 1 and 2 together with the endoscope (not shown) in the hole of the trocar 63 through the sealing member 63b located at the outer end of the trocar 63. Then, the operator moves the front-end portion of the insertion unit 14 along the large saphenous vein 62 from the opening 60d to the inguinal region 60b in the leg 60 while viewing the endoscope image. During this time, the operator manipulates the retainer manipulating slider 26 of the grip unit 16 of the blood vessel harvesting apparatus (harvester) 10 to sequentially press neighborhoods of plural portions of the large saphenous vein 62, at which the plural collateral veins 62a are branched from the large saphenous vein 62, by the blood vessel retainer 22 of the front-end portion of the insertion unit 14, and advances the cutter manipulation slider 24 of the grip unit 16 toward the insertion unit 14 to project the movable support body 17 of the cutter main unit 12 from the front-end portion of the insertion unit 14. As a result, the movable support body 17 advanced from the front-end portion of the insertion unit 14 sequentially introduces the plural branching ends of the plural collateral veins 62a into the lead passage 20a of the guide portion 20, and the bipolar cutting treatment portion 18 located at the inner end of the lead passage 20a is sequentially pressed against and cuts the introduced branching ends of the plural collaterals 62a and at the same time cauterizes the cut surfaces of the large saphenous vein 62.

Then, the operator tentatively draws the blood vessel harvesting apparatus 10 together with the endoscope from the hole of the trocar 63, and orientates the inner end of the trocar 63 toward the ankle 60a as shown by the arrow A2 of FIG. 4. The operator inserts the blood vessel harvesting apparatus (harvester) 10 together with the endoscope into the hole of the trocar 63 through the sealing member 63b located at the outer end of the trocar 63 again. Then, the operator moves the front-end portion of the insertion unit 14 along the large saphenous vein 62 from the opening 60d to the ankle 60a in the leg 60 while viewing the endoscope image. During this time, the operator manipulates the retainer manipulating slider 26 of the grip unit 16 of the blood vessel harvesting apparatus 10 to sequentially press the neighborhoods of the plural portions on the large saphenous vein 62, at which the plural collateral veins 62a are branched from the large saphenous vein 62, by the blood vessel retainer 22 of the front-end portion of the insertion unit 14, and advances the cutter manipulation slider 24 of the grip unit 16 toward the insertion unit 14 to project the movable support body 17 of the cutter main unit 12 from the front-end portion of the insertion unit 14. As a result, the movable support body 17 advanced from the front-end portion of the insertion unit 14 sequentially introduces the plural branching ends of the plural collateral veins 62a into the lead passage 20a of the guide portion 20, and the bipolar cutting treatment portion 18 located at the inner end of the lead passage 20a is sequentially pressed against and cuts the introduced branching ends of the plural collaterals 62a and at the same time cauterizes the cut surfaces of the large saphenous vein 62.

At the end of the third stage of the example of the operation method, the blood vessel harvesting apparatus (harvester) 10 together with the endoscope is drawn along with the trocar 63 from the opening 60d. Further, the both end portions of the large saphenous vein 62 are cut between the hemostatic portions of the both end portions at the opening 60e of the ankle 60a and the opening 60f of the inguinal region 60b in the leg 60, and the large saphenous vein 62 is drawn from the opening 60e of the ankle 60a or the opening 60f of the inguinal region 60b in the leg 60. Then, the opening 60a of the knee 64, the opening 60e of the ankle 60a, and the opening 60f of the inguinal region 60b of the leg 60 are closed by well-known closing means and the example of the operation method is finished.

The plural collateral veins 62a of the large saphenous vein 62 have diameters being different from each other. However, the blood vessel harvesting apparatus (harvester) 10 according to the first embodiment of the invention can change the width of the lead passage 20a formed between the capturing members 32a, 32b by moving the pair of capturing members 32a, 32b of the guide portion 20 in a direction in which the capturing members 32a, 32b intersect the lengthwise center line of the movable support body 17 (in this embodiment, the direction orthogonal to the lengthwise center line). Accordingly, the lead passage 20a can easily fit each of the plural collateral veins 62a having the different diameters, and therefore the bipolar cutting treatment portion 18 provided at the inner end of the lead passage 20a can easily cut each of the plural collateral veins 62a having the different diameters and further can easily cauterize the cut surfaces on the large saphenous vein 62.

Figure 8A:
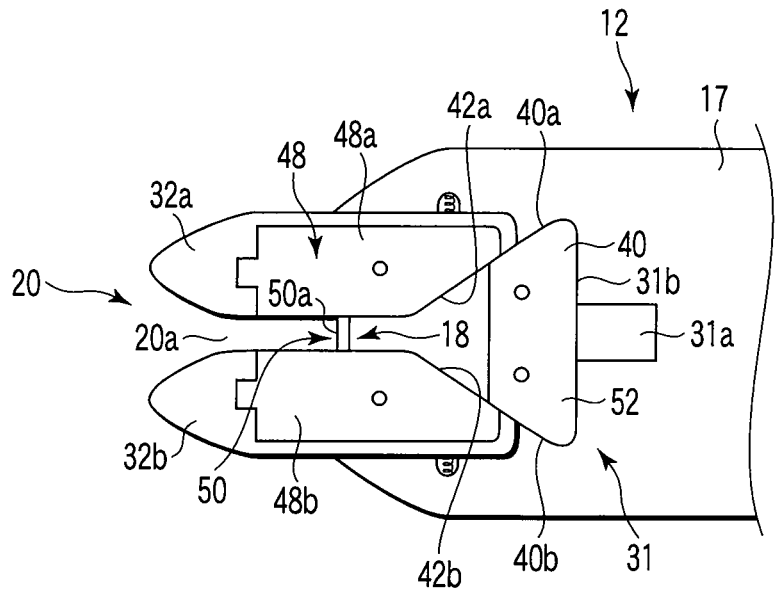
FIG. 8A is a schematic plan view showing the cutter main unit shown in FIG. 3A in a state in which a pair of capturing members 3A is brought closest to each other.

When the lead passage variable manipulation slider 44 provided in the grip unit 16 of the blood vessel harvesting apparatus (harvester) 10 shown in FIG. 1 is disposed farthest away from the insertion unit 14 in the movable range of the lead passage variable manipulation slider 44 along the lengthwise center line on the grip unit 16, the cam member 40 of the capturing member driving mechanism 31b connected to the lead passage variable manipulation slider 44 through the lengthwise moving member 31a is disposed farthest away from the front-end surface of the front-end portion of the movable support body 17 in the movable range along the lengthwise center line of the movable support body 17 in the front-end portion of the movable support body 17 as shown in FIG. 8A.

Figure 8B:
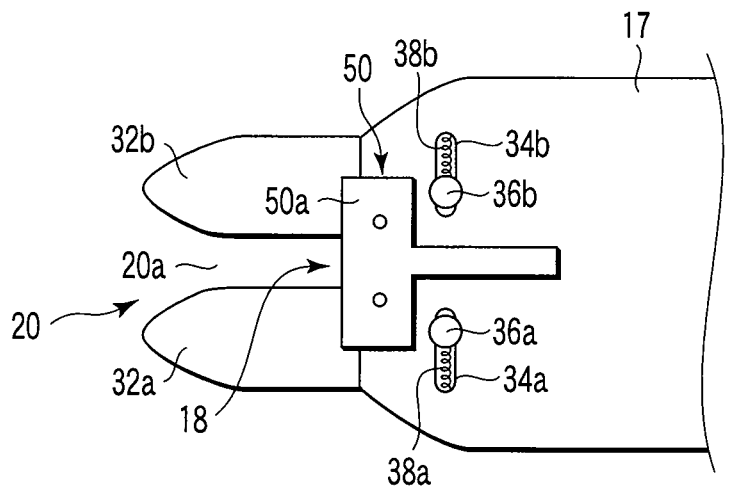
FIG. 8B is a schematic bottom view of the cutter main unit shown in FIG. 8A.

As a result, the pair of capturing members 32a, 32b of the guide portion 20 which is urged in the direction in which the lead passage 20a formed therebetween is decreased by the urging members 38a, 38b and the pair of cam sliding/contacting edges 42a, 42b of which abuts on the pair of cam surfaces 40a and 40b of the cam member 40, is disposed closest to the lengthwise center line of the movable support body 17 in the front-end portion of the movable support body 17 in the movable range in the direction intersecting the lengthwise center line of the movable support body 17 (in this embodiment, the direction which is orthogonal to the lengthwise center line) as shown in FIGS. 8A and 8B. That is, the lead passage 20a formed between the capturing members 32a, 32b has the smallest width.

When the lead passage variable manipulation slider 44 provided in the grip unit 16 of the blood vessel harvesting apparatus (harvester) 10 shown in FIG. 1 is disposed closest to the insertion unit 14 in the movable range along the lengthwise center line of the insertion unit 14 on the grip unit 16, the cam member 40 of the capturing member driving mechanism 31b connected to the lead passage variable manipulation slider 44 through the lengthwise moving member 31a is disposed closest to the front-end surface of the front-end portion of the movable support body 17 in the movable range along the lengthwise center line of the movable support body 17 on the front-end portion of the movable support body 17 as shown in FIG. 8C.

As a result, the pair of capturing members 32a, 32b of the guide portion 20, which is urged in the direction in which the lead passage 20a formed therebetween is decreased, and the pair of cam sliding/contacting edges 42a, 42b of which abut on the pair of cam surfaces 40a and 40b of the cam member 40, are disposed farthest away from the lengthwise center line in the movable range along the direction intersecting the lengthwise center line of the movable support body 17 in the front-end portion of the movable support body 17 (in this embodiment, the direction which is orthogonal to the lengthwise center line) as shown in FIGS. 8C and 8D. That is, the lead passage 20a formed between the capturing members 32a and 32b has the largest width.

This means that, by disposing the lead passage variable manipulation slider 44 provided in the grip unit 16 of the blood vessel harvesting apparatus (harvester) 10 shown in FIG. 1 at any position in the movable range along the lengthwise center line of the insertion unit 14 on the grip unit 16, the pair of capturing members 32a, 32b of the guide portion 20 can be disposed at any position in the movable range along the direction intersecting the lengthwise center line of the movable support body 17 in the front-end portion of the movable support body 17 (in this embodiment, the direction which is orthogonal to the lengthwise center line), and therefore the width of the lead passage 20a formed between the capturing members 32a, 32b can be set arbitrarily in the range between the smallest width shown in FIGS. 8A and 8B and the largest width shown in FIGS. 8C and 8D.

Further, the width of the lead passage 20a corresponding to the position of the lead passage variable manipulation slider 44 on the grip unit 16 can be recognized easily by the lead passage width index 46 disposed adjacent to the lead passage variable manipulation slider 44 on the outer surface of the grip unit 16.

Immediately before the branching end of the collateral vein 62a is introduced into the lead passage 20a, the width of the lead passage 20a can be set to the width corresponding to the diameter of the branching end of the collateral vein 62a to be introduced into the lead passage 20a, and then the branching end of the collateral vein 62a can be introduced into the lead passage 20a. Alternatively, the width of the lead passage 20a is set slightly larger than the diameter of the branching end of the collateral vein 62a to be introduced into the lead passage 20a, and then the width of the lead passage 20a can be set to the width corresponding to the diameter of the branching end of the collateral vein 62a introduced into the lead passage 20a after the branching end of the collateral vein 62a is introduced into the lead passage 20a.

Thus, since the width of the lead passage 20a can be set to the width corresponding to the diameter of the branching end of the collateral vein 62a to be introduced into the lead passage 20a, the pair of conductive terminal members 48a, 48b of the application electrode 48, which covers the pair of facing edges of the pair of capturing members 32a, 32b forming the lead passage 20a therebetween, and the conductive terminal member 50a of the return electrode 50, which covers the front end (i.e., the inner end of the lead passage 20a) of the front-end portion of the movable support body 17, can be pressed surely against the branching end of the collateral vein 62a introduced into the inner end of the lead passage 20a. As a result, the branching end of the collateral vein 62a introduced into the inner end of the lead passage 20a can be cut in the bipolar cutting treatment portion 18 at the inner end of the lead passage 20a by the high-frequency current passed from the pair of conductive terminal members 48a, 48b of the application electrode 48 to the conductive terminal member 50a of the return electrode 50, and the cut surface can be cauterized (that is, stop bleeding).

Therefore, the blood vessel harvesting operation described above with reference to FIGS. 4 to 7 can be performed quickly and the operated point in the patient body is early recovered after the operation.

[Second Embodiment]

Next, a blood vessel harvesting apparatus (harvester) 10 according to a second embodiment of the bipolar cutter of the invention will be described with reference to FIGS. 9A to 9D. A most part of a configuration of the blood vessel harvesting apparatus (harvester) 10 according to the second embodiment is the same as that of the configuration of the blood vessel harvesting apparatus (harvester) 10 according to the first embodiment described above with reference to FIGS. 1 to 8D. Accordingly, the same components of the blood vessel harvesting apparatus (harvester) 10 according to the second embodiment as those of the blood vessel harvesting apparatus (harvester) 10 according to the first embodiment are designated by the same reference numerals as those designating the same components of the blood vessel harvesting apparatus (harvester) 10 according to the first embodiment, and the detailed descriptions thereof are omitted.

The blood vessel harvesting apparatus (harvester) 10 according to the second embodiment differs from the blood vessel harvesting apparatus (harvester) 10 according to the first embodiment in the configuration of the cutter main unit 12.

In this cutter main unit 12, a pair of capturing members 32'a, 32'b of the guide portion 20 provided in and projected from the front-end portion of the movable support body 17 is rotational with respect to the front-end portion of the movable support body 17 in order to be able to vary the width of the lead passage 20a formed between the capturing members 32'a, 32'b. Particularly, portions of the base-end portions of the capturing members 32'a, 32'b facing each other are rotationally supported in the front-end portion of the movable support body 17 by a rotation center pin 74 in a state in which the portions are overlapped with each other.

Each of the capturing members 32'a, 32'b is made of a nonconductive material, and each projected end portion of the capturing members 32a, 32b is dully pointed. The edges of the base-end portions of the capturing members 32'a, 32'b facing each other are formed as inclined surfaces which are gradually separated from each other toward the end face of the base-end portion, but are different from the edges of the base-end portions of the capturing members 32a, 32b of the first embodiment facing each other and formed as the pair of inclined cam sliding/contacting edges 42a, 42b.

A pair of conductive terminal members 48'a, 48'b of the application electrode 48 of the bipolar cutting treatment portion 18, fixed to the pair of capturing members 32'a, 32'b, contacts the rotation center pin 74. The rotation center pin 74 is made of a conductive material. A first lead wire 76 extends from the front-end portion to the base-end portion in the movable support body 17, and the base-end portion of the rotation center pin 74 is electrically connected to one end portion of the first lead wire 76 located in the front-end portion of the movable support body 17.

In this embodiment, the high-frequency power supply connection cable 56 (see FIGS. 1 and 2) is not connected to the lengthwise moving member 31a of the lead passage variable manipulation portion 31, but the high-frequency power supply connection cable 56 (see FIGS. 1 and 2) is connected to the other end portion of the first lead wire 76 located in the grip unit 16.

In order to rotate the pair of capturing members 32'a, 32'b in the front-end portion of the movable support body 17 to vary the width of the lead passage 20a, the lead passage variable manipulation portion 31a interposes a link mechanism 78 between one end portion of the lengthwise moving member 31a located in the front-end portion of the movable support body 17 and the base-end portions of the pair of capturing members 32'a, 32'b. The link mechanism 78 includes a pair of link members 78a, 78b each of which has both end portions rotationally coupled to the one end portion of the lengthwise moving member 31a and each base-end portion of the capturing members 32'a, 32'b, and provides the capturing member driving mechanism 31b for driving the at least one of the capturing members 32a, 32b (in this embodiment, both the capturing members 32a, 32b) in accordance with the movement of the lengthwise moving member 31a to vary the width of the lead passage 20a.

The blood vessel harvesting apparatus (harvester) 10 according to the second embodiment of the invention rotates the pair of capturing members 32'a, 32'b of the guide portion 20 in the direction intersecting the lengthwise center line of the movable support body 17, so that the width of the lead passage 20a formed between the capturing members 32'a, 32'b can be changed. Accordingly, the lead passage 20a can be fit easily each of the plural collateral veins 62a of the large saphenous vein 62 having the different diameters and shown in FIG. 7, and therefore the bipolar cutting treatment portion 18 provided at the inner end of the lead passage 20a can easily cut each of the plural collateral veins 62a having the different diameters and can cauterize the cut surface easily.

When the lead passage variable manipulation slider 44 provided in the grip unit 16 of the blood vessel harvesting apparatus (harvester) 10 shown in FIG. 1 is disposed farthest away from the insertion unit 14 in the movable range along the lengthwise center line on the grip unit 16, the pair of link members 78a, 78b of the link mechanism 78 of the capturing member driving mechanism 31b connected to the lead passage variable manipulation slider 44 through the lengthwise moving member 31a disposes the pair of capturing members 32'a, 32'b at positions being closest to the lengthwise center line in the rotational range in a direction in which the pair of capturing members 32'a, 32'b intersects the lengthwise center line of the movable support body 17 in the front-end portion of the movable support body 17 as shown in FIGS. 9A and 9B. That is, the lead passage 20a formed between the capturing members 32'a, 32'b has the smallest width.

Figure 9C:
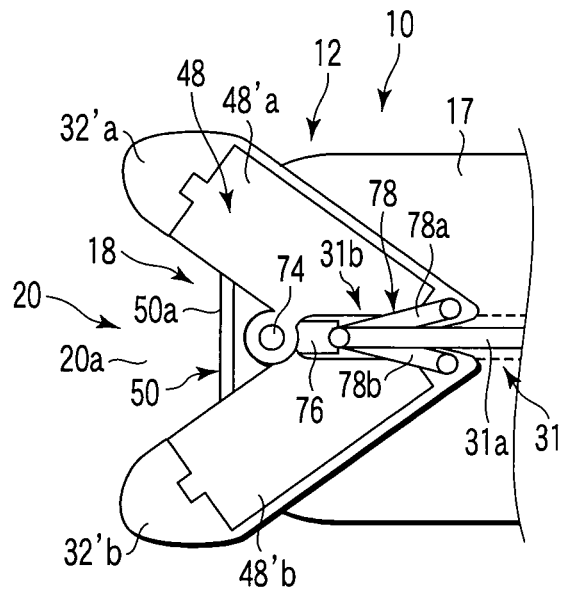
FIG. 9C is a schematic plan view showing the cutter main unit shown in FIG. 9A in a state in which the pair of capturing members is kept farthest away from each other.
Figure 9D:
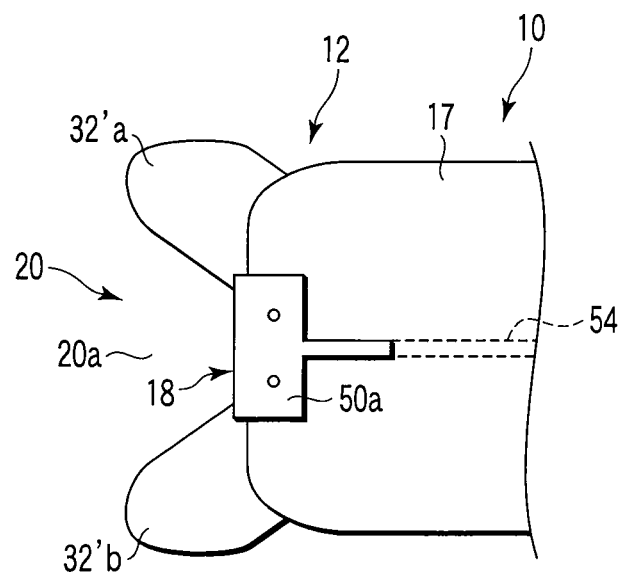
FIG. 9D is a schematic bottom view of the cutter main unit shown in FIG. 9C.

When the lead passage variable manipulation slider 44 provided in the grip unit 16 of the blood vessel harvesting apparatus (harvester) 10 shown in FIG. 1 is disposed closest to the insertion unit 14 in the movable range along the lengthwise center line of the insertion unit 14 on the grip unit 16, the pair of link members 78a, 78b of the link mechanism 78 of the capturing member driving mechanism 31b connected to the lead passage variable manipulation slider 44 through the lengthwise moving member 31a disposes the pair of capturing members 32'a, 32'b at positions being farthest away from the lengthwise center line in the rotational range in the direction in which the pair of capturing members 32'a, 32'b intersects the lengthwise center line of the movable support body 17 in the front-end portion of the movable support body 17 as shown in FIGS. 9C and 9D. That is, the lead passage 20a formed between the capturing members 32'a, 32'b has the largest width.

This means that, by disposing the lead passage variable manipulation slider 44 provided in the grip unit 16 of the blood vessel harvesting apparatus (harvester) 10 shown in FIG. 1 at any position in the movable range along the lengthwise center line of the insertion unit 14 on the grip unit 16, the pair of capturing members 32'a, 32'b of the guide portion 20 can be disposed at any position in the movable range along the direction intersecting the lengthwise center line of the movable support body 17 in the front-end portion of the movable support body 17, and therefore the width of the lead passage 20a formed between the capturing members 32'a, 32'b can be set arbitrarily in the range between the smallest width shown in FIGS. 9A and 9B and the largest width shown in FIGS. 9C and 9D.

Further, the width of the lead passage 20a corresponding to the position of the lead passage variable manipulation slider 44 in the grip unit 16 can be recognized easily by the lead passage width index 46 disposed adjacent to the lead passage variable manipulation slider 44 on the outer surface of the grip unit 16 as shown in FIG. 3A.

Immediately before the branching end of the collateral vein 62a is introduced into the lead passage 20a, the width of the lead passage 20a can be set to the width corresponding to the diameter of the branching end of the collateral vein 62a to be introduced into the lead passage 20a, and then the branching end of the collateral vein 62a can be introduced into the lead passage 20a. Alternatively, the width of the lead passage 20a is set slightly larger than the diameter of the branching end of the collateral vein 62a to be introduced into the lead passage 20a, and then the width of the lead passage 20a can be set to the width corresponding to the diameter of the branching end of the collateral vein 62a introduced into the lead passage 20a after the branching end of the collateral vein 62a is introduced into the lead passage 20a.

Thus, since the width of the lead passage 20a can be set to the width corresponding to the diameter of the branching end of the collateral vein 62a to be introduced into the lead passage 20a, the pair of conductive terminal members 48'a, 48'b of the application electrode 48, which covers the pair of facing edges of the pair of capturing members 32'a, 32'b forming the lead passage 20a therebetween, and the conductive terminal member 50a of the return electrode 50, which covers the front end (i.e., the inner end of the lead passage 20a) of the front-end portion of the movable support body 17, can be pressed surely against the branching end of the collateral vein 62a introduced into the inner end of the lead passage 20a. As a result, the branching end of the collateral vein 62a introduced into the inner end of the lead passage 20a can be cut in the bipolar cutting treatment portion 18 at the inner end of the lead passage 20a by the high-frequency current passed from the pair of conductive terminal members 48'a, 48'b of the application electrode 48 to the conductive terminal member 50a of the return electrode 50, and the cut surface can be cauterized (that is, stop bleeding).

Therefore, the blood vessel harvesting operation described above with reference to FIGS. 4 to 7 can be performed quickly and the operated point in the patient body is early recovered after the operation.

In this embodiment, the pair of capturing members 32'a, 32'b is not urged toward the direction in which the width of the lead passage 20a formed between the capturing members 32'a, 32'b is decreased. However, the pair of capturing members 32'a, 32'b can be urged in this manner by bridging the well-known urging member between the pair of capturing members 32'a, 32'b. For example, as shown by a two-dots chain line in FIG. 9A, the well-known urging member can be provided by a torsion coil spring 79 which is wounded on the rotation center pin 74 and which has two legs engaged with the base-end portions of the capturing members 32'a, 32'b.

[Third Embodiment]

Next, a blood vessel harvesting apparatus (harvester) 10 according to a third embodiment of the bipolar cutter of this invention will be described with reference to FIGS. 10A and 10B.

Similarly to the blood vessel harvesting apparatus (harvester) 10 according to the first embodiment shown in FIG. 1, the blood vessel harvesting apparatus (harvester) 10 includes the insertion unit 14 inserted in the body of the living thing (in this embodiment, in the leg of the human), the bipolar cutting treatment portion 18 provided in the front-end portion of the insertion unit 14, and the guide portion 20 including the lead passage which is provided in the front-end portion of the insertion unit 14, which captures the living tissue (in this embodiment, the blood vessel) of the cutting target in the body of the living thing and guides the living tissue to the bipolar cutting treatment portion 18.

The blood vessel harvesting apparatus (harvester) 10 differs from the blood vessel harvesting apparatus (harvester) 10 according to the first embodiment shown in FIG. 1 in the configuration of the cutter main unit 12 provided in the front-end portion of the movable support body 17 in the front-end portion of the insertion unit 14.

The guide portion 20 of this embodiment includes at least three capturing members 82a, 82b, and 82c (in this embodiment, three capturing members) which are formed in the front-end surface of the front-end portion of the movable support body 17 to extend in parallel with each other along the lengthwise center line of the movable support body 17 from at least three positions (in this embodiment, three positions) separated from each other in the direction orthogonal to the lengthwise center line of the movable support body 17. Plural lead passages 84a, 84b (in this embodiment, two lead passages) are formed between the at least three capturing members 82a, 82b, and 82c (in this embodiment, three capturing members).

The plural lead passages 84a, 84b (in this embodiment, two lead passages) have different widths. Each front-end portion of the at least three capturing members 82a, 82b, and 82c (in this embodiment, three capturing members) is formed in a dully pointed shape. Further, in the this embodiment, an extending length of the capturing member 82b located in the center is longer than an extending length of each of the two capturing members 82a, 82c located on both sides of the capturing member 82b.

The bipolar cutting treatment portion 18 includes an application electrode 86 fixed to the at least three capturing members 82a, 82b, and 82c (in this embodiment, three capturing members) and a return electrode 88 fixed to the front-end portion of the movable support body 17.

In one surface of each of at least the three capturing members 82a, 82b, and 82c (in the third embodiment, three capturing members), the application electrode 86 extends along or the neighborhoods of the facing edges which regulate each of the lead passages 84a, 84b respectively, and is electrically connected to one end portion of a first lead wire 90 in the front-end portion of the movable support body 17. The first lead wire 90 extends from the front-end portion to the base-end portion of the movable support body 17 in the movable support body 17.

The return electrode 88 is exposed at the inner end of each of the plural lead passages 84a, 84b (in this embodiment, two lead passages) in the front-end portion of the movable support body 17, and is electrically connected to one end portion of a second lead wire 92. The second lead wire 92 extends from the front-end portion to the base-end portion of the movable support body 17 in the movable support body 17.

The high-frequency power supply connection cable 56 is connected to the other end portion of the first lead wire 90 for the application electrode 86 and the other end portion of the second lead wire 92 for the return electrode 88 in the base-end portion of the movable support body 17 in the grip unit 16 (see FIG. 1).

In this embodiment, since each of the at least three capturing members 82a, 82b, and 82c (in this embodiment, three capturing members) is not moved with respect to the front-end portion of the movable support body 17, the blood vessel harvesting apparatus (harvester) 10 of this embodiment includes neither the lead passage variable manipulation slider 44 shown in FIGS. 1 and 3A nor the lengthwise moving member 31a and capturing member driving mechanism 31b of the lead passage variable manipulation portion 31 shown in FIG. 3A.

Figure 10A:
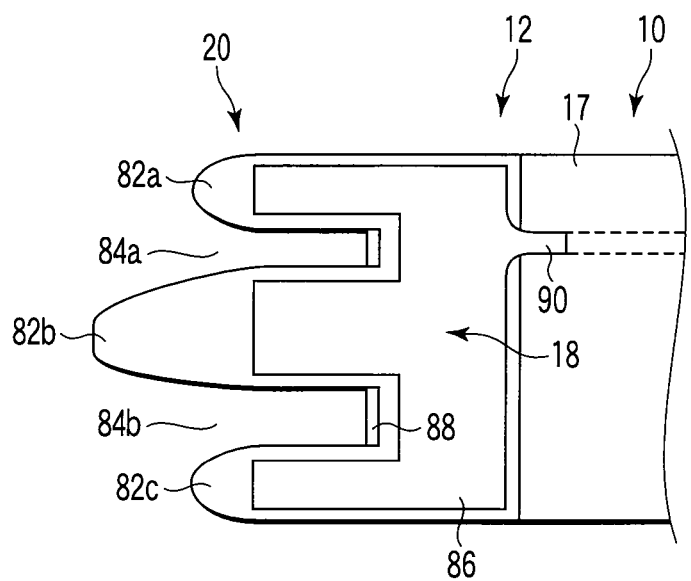
FIG. 10A is a schematic plan view showing a cutter main unit of a blood vessel harvesting apparatus (harvester) according to a third embodiment of the bipolar cutter of the present invention.
Figure 10B:
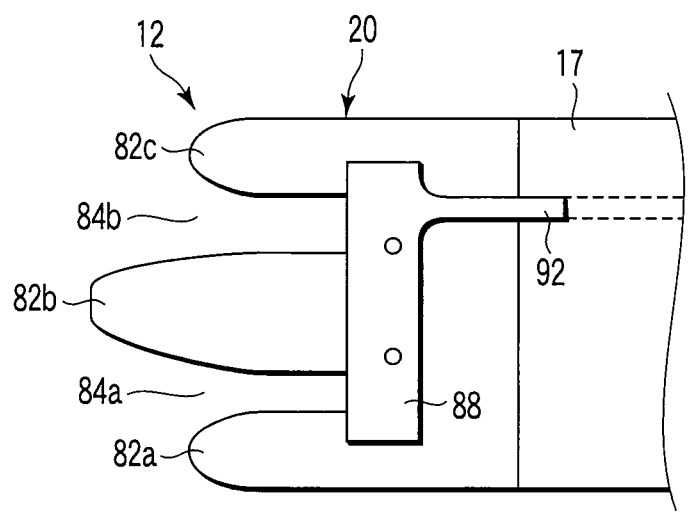
FIG. 10B is a schematic bottom view of the cutter main unit shown in FIG. 10A.

Accordingly, in comparison with the blood vessel harvesting apparatus (harvester) 10 of the first embodiment, the configuration of the cutter main unit 12 of which is shown in FIGS. 3A to 3C, and the blood vessel harvesting apparatus (harvester) 10 of the second embodiment, the configuration of the cutter main unit 12 of which is shown in FIGS. 9A to 9D, the blood vessel harvesting apparatus (harvester) 10 of this embodiment, the configuration of the cutter main unit 12 of which is shown in FIGS. 10A and 10B, has a simple configuration.

In the blood vessel harvesting apparatus (harvester) 10 of the third embodiment, the movable support body 17 of the insertion unit 14 is manipulated such that the branching end of the collateral vein 62a to be cut is introduced into the lead passage 84a or 84b having the width corresponding to the diameter of the branching end of the collateral vein 62a to be cut as shown in FIG. 5. As a result, the application electrode 86, which is along the edges of the two capturing members 82a, 82b, or 82b, 82c facing each other and forming the lead passage 84a or 84b therebetween, and the return electrode 88, which is exposed at the inner end of each of the lead passages 84a and 84b in the front end of the front-end portion of the movable support body 17, can be surely brought close to or pressed against the branching end of the collateral vein 62a introduced into the lead passage 84a or 84b. Then, the branching end of the collateral vein 62a introduced into the inner end of the lead passage 84a or 84b can be cut in the bipolar cutting treatment portion 18 at the inner end of the lead passage 84a or 84b by an high-frequency current passed from the application electrode 86 to the return electrode 88, and the cut surface can be cauterized (i.e., stop bleeding).

Therefore, the blood vessel harvesting operation described above with reference to FIGS. 4 to 7 can be performed quickly and the operated point in the patient body is early recovered after the operation.

[Fourth Embodiment]

Next, a blood vessel harvesting apparatus (harvester) 10 according to a fourth embodiment of the bipolar cutter of this invention will be described with reference to FIGS. 11A to 11D.

Similarly to the blood vessel harvesting apparatus (harvester) 10 of the first embodiment shown in FIG. 1, the blood vessel harvesting apparatus (harvester) 10 of the fourth embodiment includes the insertion unit 14 inserted in a body of a living thing (in the fourth embodiment, in a leg of a human), the bipolar cutting treatment portion 18 provided on the front-end portion of the insertion unit 14, and the guide portion 20 including the lead passage provided in the front-end portion of the insertion unit 14. The lead passage captures the living tissue (in the fourth embodiment, the blood vessel) of the cutting target in the living body and guides the living tissue to the bipolar cutting treatment portion 18.

The blood vessel harvesting apparatus (harvester) 10 of the fourth embodiment differs from the blood vessel harvesting apparatus (harvester) 10 of the first embodiment shown in FIG. 1 in the configuration of the cutter main unit 12 provided on the front-end portion of the movable support body 17 in the front-end portion of the insertion unit 14.

In the cutter main unit 12 of the fourth embodiment, as shown in FIGS. 11A and 11B, the guide portion 20 provided on the front-end portion of the movable support body 17 includes a pair of capturing members 102a, 102b projecting outward from the front-end portion in parallel with each other along the lengthwise direction of the movable support body 17. The capturing members 102a, 102b form the lead passage 20a therebetween. Each of the capturing members 102a, 102b is made of the nonconductive material, and each projecting end portion of the capturing members 102a, 102b is dully pointed. As a result, the outer end portion of the lead passage 20a corresponding to projecting end portions of the capturing members 102a, 102b is gradually broadened in its width toward the outer end thereof. Each base-end surface of the base-end portions of the capturing members 102a, 102b extends in a direction intersecting the lengthwise center line of the movable support body 17 (in the fourth embodiment, the direction orthogonal to the lengthwise center line).

At least one of the capturing members 102a, 102b (in the fourth embodiment, both the capturing members 102a, 102b) is provided on the front-end portion of the movable support body 17 so as to be movable in parallel to the lengthwise center line of the movable support body 17 in the direction intersecting the lengthwise center line (in the fourth embodiment, the direction orthogonal to the lengthwise center line), and is urged toward the direction in which the width of the lead passage 20a formed between the capturing members 102a, 102b is decreased.

Particularly, a pair of guide grooves 104a, 104b whose planar shape is formed in a square is formed in a pair of regions on the front-end portion of the movable support body 17 corresponding to the base-end portions of the pair of capturing members 102a, 102b. In four sides of each planar shape of the guide grooves 104a, 104b, one side located far away from the front-end surface of the front-end portion of the movable support body 17 is formed as a guide surface extending in a direction intersecting the lengthwise center line of the movable support body 17 (in the fourth embodiment, the direction orthogonal to the lengthwise center line).

A pair of sliding members 106a, 106b inserted in the pair of guide grooves 104a, 104b in the pair of regions of the front-end portion of the movable support body 17 is fixed to the base-end portions of the capturing members 102a, 102b. Each planar shape of the sliding members 106a, 106b is also formed in the square. And, in four sides of each planar shape of the sliding members 106a, 106b, one side located far away from the front-end surface of the front-end portion of the movable support body 17 is formed as a sliding surface extending in a direction intersecting the lengthwise center line of the movable support body 17 (in the fourth embodiment, the direction orthogonal to the lengthwise center line). Each of the sliding members 106a, 106b can be moved in the direction intersecting the lengthwise center line of the movable support body 17 (in the fourth embodiment, the direction orthogonal to the lengthwise center line) in each of the guide grooves 104a, 104b while each sliding surface is sliding on the guide surface of each of the guide grooves 104a, 104b.

Urging members 108 such as compression coil springs are disposed in the pair of guide grooves 104a, 104b of the pair of regions on the front-end portion of the movable support body 17 to urge the pair of sliding members 106a, 106b inserted in the pair of guide grooves 104a, 104b such that the sliding members 106a, 106b are closed to the lengthwise center line of the movable support body 17. This means that the urging members 108 urge the pair of capturing members 102a, 102b so as to decrease the width of the lead passage 20a formed between the capturing members 102a, 102b.

The bipolar cutting treatment portion 18 provided in the front-end portion of the movable support body 17 includes a pair of electrodes, i.e., an application electrode 110 and a return electrode 112, which are provided in the front-end portion of the movable support body 17.

The application electrode 110 includes a pair of conductive terminal members 110a, 110b fixed to the pair of capturing members 102a, 102b. The pair of conductive terminal members 110a, 110b covers the pair of facing edges forming the lead passage 20a therebetween and the pair of base-end edges of the base-end portions on the capturing members 102a, 102b.

The return electrode 112 includes a conductive terminal member 112a fixed to the front-end portion of the movable support body 17. The conductive terminal member 112a covers a size larger than the maximum width of the lead passage 20a formed between the capturing members 102a, 102b, at the front end of the front-end portion of the movable support body 17. This means that the conductive terminal member 112a is disposed at the inner end of the lead passage 20a.

An intermediate conductive terminal member 114 is also disposed on the front-end portion of the movable support body 17, and extends in the direction intersecting the lengthwise center line of the movable support body 17 (in the fourth embodiment, the direction orthogonal to the lengthwise center line) along the base-end surface of each base-end portion of the capturing members 102a, 102b. The pair of conductive terminal members 110a, 110b of the application electrode 110 which covers the base-end surface of each base-end portion of the capturing members 102a, 102b contacts the intermediate conductive terminal member 114. Accordingly, the intermediate conductive terminal member 114 is electrically connected to the pair of conductive terminal members 110a, 110b of the application electrode 110.

The intermediate conductive terminal member 114 is also electrically connected to a first lead wire 116 extending along the lengthwise direction of the movable support body 17 in the movable support body 17. The other end portion of the first lead wire 116 is exposed on the other end portion of the movable support body 17 disposed in the grip unit 16 (see FIGS. 1 and 2).

The conductive terminal member 112a of the return electrode 112 is electrically connected to one end portion of a second lead wire 118 extending along the lengthwise direction of the movable support body 17 in the movable support body 17. The other end portion of the second lead wire 118 is exposed on the other end portion of the movable support body 17 disposed in the grip unit 16 (see FIGS. 1 and 2).

In the grip unit 16, the other end portion of the first lead wire 116 for the pair of conductive terminal members 110a and 110b of the application electrode 110, exposed on the other end portion of the movable support body 17, and the other end portion of the second lead wire 118 for the return electrode 112, exposed on the other end portion of the movable support body 17 are electrically connected to one end portion of the high-frequency power supply connection cable 56 (see FIGS. 1 and 2).

The blood vessel harvesting apparatus (harvester) 10 of the fourth embodiment includes neither the lead passage variable manipulation slider 44 shown in FIGS. 1 and 3A nor the lengthwise moving member 31a and capturing member driving mechanism 31b (cam member 40) of the lead passage variable manipulation portion 31 shown in FIG. 3A.

Accordingly, the blood vessel harvesting apparatus (harvester) 10 of the fourth embodiment, the configuration of the cutter main unit 12 of which is shown in FIGS. 11A and 11B, has more simple configuration in comparison with the blood vessel harvesting apparatus (harvester) 10 of the first embodiment, the configuration of the cutter main unit 12 of which is shown in FIGS. 3A to 3C, and the blood vessel harvesting apparatus (harvester) 10 of the second embodiment, the configuration of the cutter main unit 12 of which is shown in FIGS. 9A to 9D.

In FIGS. 11A and 11B, the capturing members 102a, 102b of the blood vessel harvesting apparatus (harvester) 10 of the fourth embodiment are disposed at positions closest to each other by the urging forces of the urging members 108, and the width of the lead passage 20a formed between the capturing members 102a, 102b becomes narrowest at that time.

Figure 11C:
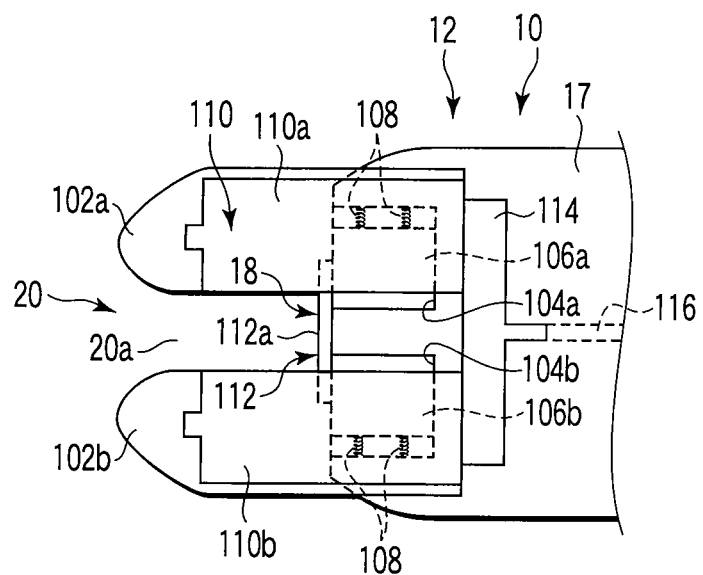
FIG. 11C is a schematic plan view showing the cutter main unit shown in FIG. 11A in a state in which the pair of capturing members is kept farthest away from each other.
Figure 11D:
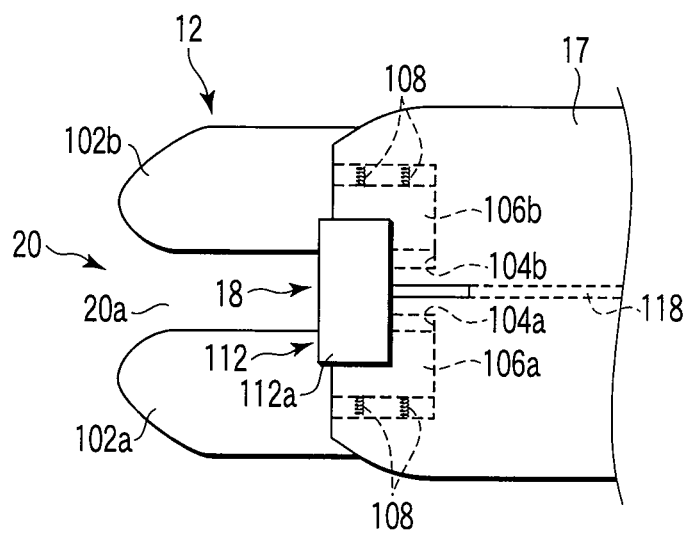
FIG. 11D is a schematic bottom view of the cutter main unit shown in FIG. 11C.

Further, in FIGS. 11C and 11D, the capturing members 102a, 102b of the blood vessel harvesting apparatus (harvester) 10 of the fourth embodiment are disposed at positions farthest away from each other against the urging forces of the urging members 108, and the width of the lead passage 20a formed between the capturing members 102a, 102b becomes broadest at that time.

In the blood vessel harvesting apparatus (harvester) 10 of the fourth embodiment, the movable support body 17 of the insertion unit 14 is manipulated such that the branching end of the collateral vein 62a to be cut as shown in FIG. 5 is introduced into the lead passage 20a. When the diameter of the branching end of the collateral vein 62a introduced into the lead passage 20a is larger than the narrowest width of the lead passage 20a formed between the capturing members 102a, 102b, the pair of capturing members 102a, 102b is pressed by the branching end of the collateral vein 62a introduced into the lead passage 20a, and is opened in the direction in which the capturing members 102a, 102b are separated from each other against the urging forces of the urging members 108. As a result, the width of the lead passage 20a formed between the capturing members 102a, 102b is automatically adjusted in accordance with the diameter of the branching end of the collateral 62a introduced into the lead passage 20a.

The automatic adjustment of the width of the lead passage 20a formed between the capturing members 102a, 102b is performed in a range of the diameter of the branching end of the collateral vein 62a introduced into the lead passage 20a between the narrowest width of the lead passage 20a shown in FIGS. 11A and 11B and the broadest width of the lead passage 20a shown in FIGS. 11C and 11D.

As a result, the pair of conductive terminal members 110a, 110b of the application electrode 110 along the facing edges of the two capturing members 102a, 102b forming the lead passage 20a therebetween and the conductive terminal member 112a of the return electrode 112 exposed on the inner end of the lead passage 20a at the front end of the front-end portion of the movable support body 17 can surely be brought close to or pressed against the branching end of the collateral vein 62a introduced into the lead passage 20a. Then, the branching end of the collateral vein 62a introduced into the inner end of the lead passage 20a can be cut by the high-frequency current passed from the pair of conductive terminal members 110a, 110b of the application electrode 110 to the conductive terminal member 112a of the return electrode 112 and the cut surface can be cauterized (i.e., stop bleeding) in the bipolar cutting treatment portion 18 at the inner end of the lead passage 20*a*.

Therefore, the blood vessel harvesting operation described with reference to FIGS. 4 to 7 can be performed quickly and the operated point in the patient body is early recovered after the operation.

[Fifth Embodiment]

A blood vessel harvesting apparatus (harvester) 10 according to a fifth embodiment of the bipolar cutter of this invention will be described with reference to FIGS. 12A to 12D.

Similarly to the blood vessel harvesting apparatus (harvester) 10 of the first embodiment shown in FIG. 1, the blood vessel harvesting apparatus (harvester) 10 of the fifth embodiment includes the insertion unit 14 inserted in the body of the living thing (in the fifth embodiment, in the leg of the human), the bipolar cutting treatment portion 18 provided in the front-end portion of the insertion unit 14, and the guide portion 20 including the lead passage provided in the front-end portion of the insertion unit 14 to capture the living tissue (in the fifth embodiment, the blood vessel) of the cutting target in the body of the living thing and to guide the living tissue to the bipolar cutting treatment portion 18.

The blood vessel harvesting apparatus (harvester) 10 of the fifth embodiment differs from the blood vessel harvesting apparatus (harvester) 10 of the first embodiment shown in FIG. 1 in the configuration of the cutter main unit 12 provided in the front-end portion of the movable support body 17 in the front-end portion of the insertion unit 14.

Figure 12A:
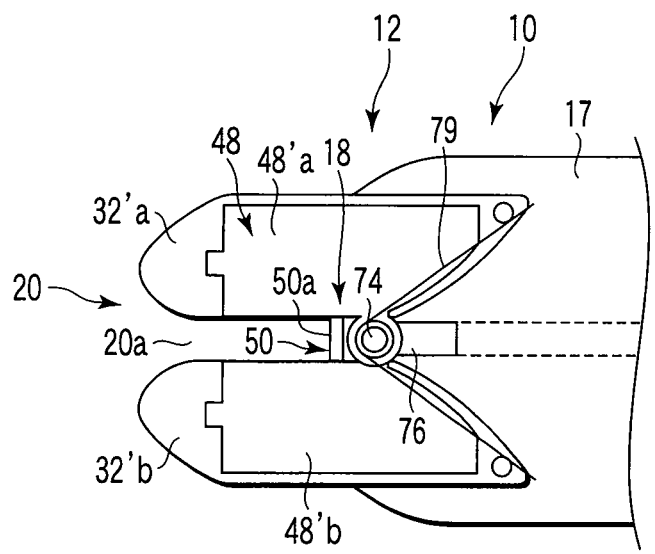
FIG. 12A is a schematic plan view showing a cutter main unit of a blood vessel harvesting apparatus (harvester) according to a fifth embodiment of the bipolar cutter of the present invention in a state in which a pair of capturing members is brought closest to each other.
Figure 12B:
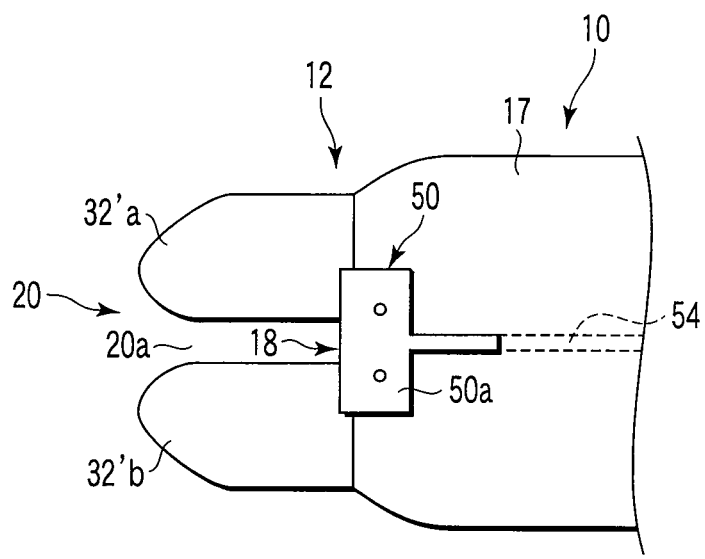
FIG. 12B is a schematic bottom view of the cutter main unit shown in FIG. 12A.

As shown in FIGS. 12A and 12B, the cutter main unit 12 of the fifth embodiment is configured by removing the lead passage variable manipulation portion 31 from the blood vessel harvesting apparatus (harvester) 10 of the second embodiment shown in FIGS. 9A and 9D and by urging the pair of capturing members 32'*a*, 32'*b* provided in the movable support body 17 in the guide portion 20 to be rotational about the rotation center pin 74 such that the width of the lead passage 20*a* formed between the capturing members 32'*a*, 32'*b* is decreased. Urging of the pair of capturing members 32'*a*, 32'*b* can be performed by bridging the well-known urging member between the pair of capturing members 32'*a*, 32'*b*, as described in the blood vessel harvesting apparatus (harvester) 10 of the second embodiment. For example, as shown by the two-dots chain line in FIG. 9A and by a solid line in FIG. 12A, the well-known urging member can be provided by a torsion coil spring 79 which is wounded around the rotation center pin 74 and which has two legs engaged with the base-end portions of the capturing members 32'*a*, 32'*b*.

The blood vessel harvesting apparatus (harvester) 10 of the fifth embodiment includes neither the lead passage variable manipulation slider 44 shown in FIGS. 1 and 3A nor the lengthwise moving member 31*a* and capturing member driving mechanism 31*b* (the link members 78*a*, 78*b* of the ink mechanism 78) of the lead passage variable manipulation portion 31 shown in FIG. 9A.

Accordingly, the blood vessel harvesting apparatus (harvester) 10 of the fifth embodiment, the configuration of the cutter main unit 12 of which is shown in FIGS. 12A and 12B, has more simple configuration in comparison with the blood vessel harvesting apparatus (harvester) 10 of the first embodiment, the configuration of the cutter main unit 12 of which is shown in FIGS. 3A to 3C, and the blood vessel harvesting apparatus (harvester) 10 of the second embodiment, the configuration of the cutter main unit 12 of which is shown in FIGS. 9A to 9D.

In FIGS. 12A and 12B, the front-end portions of the capturing members 32'*a*, 32'*b* of the blood vessel harvesting apparatus (harvester) 10 of the fifth embodiment are disposed at positions closest to each other by the urging force of the urging member 79, and the width of the lead passage 20*a* formed between the front-end portions of the capturing members 32'*a*, 32'*b* becomes narrowest at that time.

Figure 12C:
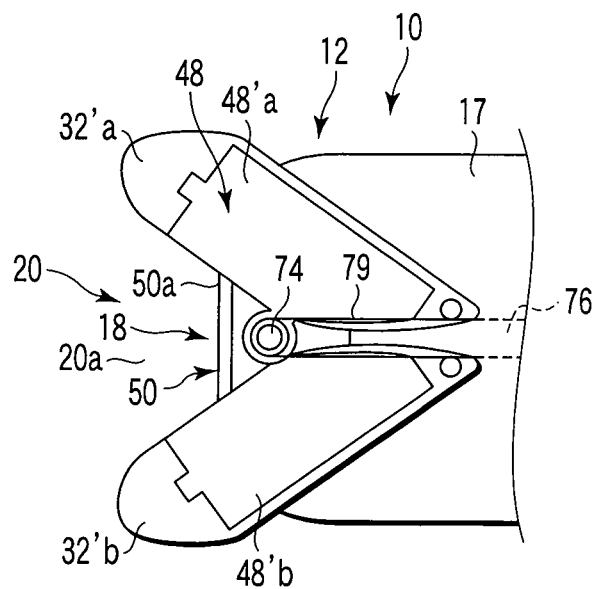
FIG. 12C is a schematic plan view showing the cutter main unit shown in FIG. 12A in a state in which the pair of capturing members is kept farthest away from each other.
Figure 12D:
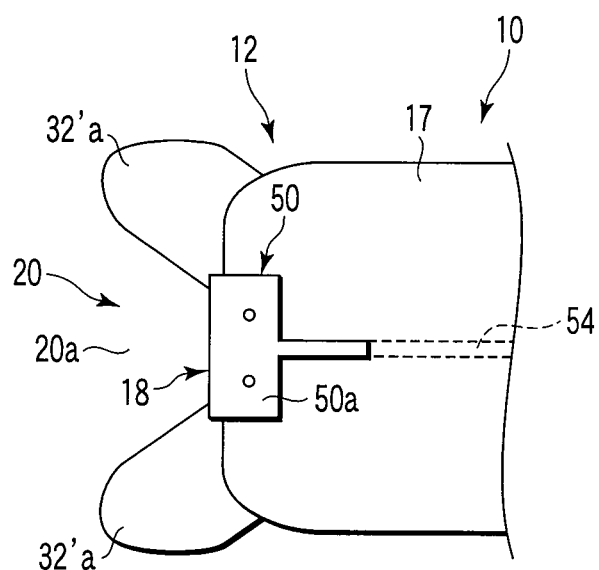
FIG. 12D is a schematic bottom view of the cutter main unit shown in FIG. 12C.

In FIGS. 12C and 12D, the front-end portions of the capturing members 32'*a*, 32'*b* of the blood vessel harvesting apparatus (harvester) 10 of the fifth embodiment are disposed at positions farthest away from each other against the urging force of the urging member 79, and the width of the lead passage 20*a* formed between the front-end portions of the capturing members 102*a* and 102*b* becomes broadest at that time.

In the blood vessel harvesting apparatus (harvester) 10 of the fifth embodiment, the movable support body 17 of the insertion unit 14 is manipulated such that the branching end of the collateral vein 62*a* to be cut as shown in FIG. 5 is introduced into the lead passage 20*a*. When the diameter of the branching end of the collateral vein 62*a* introduced into the lead passage 20*a* is larger than the narrowest width of the lead passage 20*a* formed between the capturing members 32'*a*, 32'*b*, the front-end portions of the capturing members 32'*a*, 32'*b* are pressed by the branching end of the collateral vein 62*a* introduced into the lead passage 20*a* and are opened in the direction in which the capturing members 32'*a*, 32'*b* are separated from each other against the urging force of the urging member 79. The width of the lead passage 20*a* formed between the capturing members 32'*a*, 32'*b* is automatically adjusted in accordance with the diameter of the branching end of the collateral 62*a* introduced into the lead passage 20*a*.

Such an automatic adjustment of the width of the lead passage 20*a* formed between the capturing members 32'*a*, 32'*b* in accordance with the diameter of the branching end of the collateral vein 62*a* introduced into the lead passage 20*a* is performed in a range of the diameter of the branching end of the collateral 62*a* between the narrowest width of the lead passage 20*a* shown in FIGS. 12A and 12B and the broadest width of the lead passage 20*a* shown in FIGS. 12 C and 12D.

As a result, the pair of conductive terminal members 48'*a*, 48'*b* of the application electrode 48 along the facing edges of the two capturing members 32'*a*, 32'*b* forming the lead passage 20*a* therebetween and the conductive terminal member 50*a* of the return electrode 50 exposed on the inner end of the lead passage 20*a* in the front end of the front-end portion of the movable support body 17 can be surely brought close to or pressed against the branching end of the collateral vein 62*a* introduced into the lead passage 20*a*. Then, the branching end of the collateral vein 62*a* introduced into the inner end of the lead passage 20*a* can be cut by the high-frequency current passed from the pair of conductive terminal members 48'*a*, 48'*b* of the application electrode 48 to the conductive terminal member 50*a* of the return electrode 50 and the cut surface can be cauterized (i.e., stop bleeding) in the bipolar cutting treatment portion 18 at the inner end of the lead passage 20*a*.

Therefore, the blood vessel harvesting operation described with reference to FIGS. 4 to 7 can be performed quickly and the operated point in the patient body is early recovered after the operation.

[Sixth Embodiment]

The blood vessel harvesting apparatus (harvester) 10 according to a sixth embodiment of the bipolar cutter of the invention will be described with reference to FIGS. 13A to 13D.

Similarly to the blood vessel harvesting apparatus (harvester) 10 of the first embodiment shown in FIG. 1, the blood vessel harvesting apparatus (harvester) 10 of the sixth embodiment includes the insertion unit 14 inserted in the body of the living thing (in the sixth embodiment, in the leg of the human), the bipolar cutting treatment portion 18 provided in the front-end portion of the insertion unit 14, and the guide portion 20 including a lead passage 20'a provided in the front-end portion of the insertion unit 14 to capture the living tissue (in the sixth embodiment, the blood vessel) of the cutting target in the body of the living thing and to guide the living tissue to the bipolar cutting treatment portion 18.

The blood vessel harvesting apparatus (harvester) 10 of the sixth embodiment differs from the blood vessel harvesting apparatus (harvester) 10 of the first embodiment shown in FIG. 1 in the configuration of the cutter main unit 12 provided on the front-end portion of the movable support body 17 in the front-end portion of the insertion unit 14.

The lead passage 20'a of the guide portion 20 of this embodiment is formed in a shape in which the lead passage 20'a is enlarged as the lead passage 20'a recedes from the front-end portion of the insertion unit 14. Particularly, the guide portion 20 of the sixth embodiment includes two capturing members 132a, 132b formed in the front-end surface of the front-end portion of the movable support body 17 and extending in parallel with each other along the lengthwise center line of the movable support body 17 from two positions separated from each other in the direction orthogonal to the lengthwise center line of the movable support body 17. And, the lead passage 20'a is formed between the two capturing members 132a, 132b.

Further in this embodiment, the lead passage 20'a is formed in a substantially V-shape.

The guide portion 20 of this embodiment also includes a lead passage width regulating member 134 which can be moved between the inner end of the lead passage 20'a and a position close to the outer end of the lead passage 20'a along the lengthwise center line (i.e., the lengthwise center line of the movable support body 17) of the insertion unit 14.

The lead passage width regulating member 134 is fixed to one end portion of a lengthwise moving member 31'a having the configuration similar to that of the lengthwise moving member 31a of the lead passage width variable manipulation portion 31 shown in FIG. 3A. Similarly to the lengthwise moving member 31a of the lead passage width variable manipulation portion 31 shown in FIG. 3A, the other end portion of the lengthwise moving member 31'a is fixed to the lead passage variable manipulation slider 44 in the grip unit 16.

The bipolar cutting treatment portion 18 includes an application electrode 136 fixed to the two capturing members 132a, 132b and a return electrode 138 fixed to the lead passage width regulating member 134.

The application electrode 136 extends along facing edges regulating the lead passage 20'a or the neighborhoods of the facing edges in one surface of each of the two capturing members 132a, 132b, and is electrically connected to one end portion of a first lead wire 140 in the front-end portion of the movable support body 17. The first lead wire 140 extends from the front-end portion to the base-end portion of the movable support body 17 in the movable support body 17.

The return electrode 138 covers the front-end surface of the front-end portion of the lead passage width regulating member 134, which is flush with the front-end surface of the front-end portion of the movable support body 17, i.e., the inner end into the lead passage 20'a, or slightly projects from the inner end into the lead passage 20'a. In the front-end portion of the movable support body 17, the return electrode 138 is electrically connected to one end portion of a second lead wire (not shown) extending along the lengthwise direction of the lengthwise moving member 31'a in the lengthwise moving member 31'a. The other end portion of the second lead wire (not shown) is exposed on the other end portion of the lengthwise moving member 31'a disposed in the grip unit 16.

By making the lengthwise moving member 31'a of the conductive material, the lengthwise moving member 31'a can be used in place of the second lead wire (not shown). In this case, the lead passage variable manipulation slider 44 is made of the nonconductive material.

In the base-end portion of the movable support body 17 in the grip unit 16 (see FIG. 1), the high-frequency power supply connection cable 56 is connected to the other end portion of the first lead wire 140 for the application electrode 136 and the other end portion of the second lead wire (not shown) for the return electrode 138.

In this embodiment, each of the two capturing members 132a, 132b is not moved to the front-end portion of the movable support body 17. Instead, in the lead passage 20'a between the two capturing members 132a, 132b, the lead passage width regulating member 134 is moved along the lengthwise center line of the movable support body 17 between the inner end of the lead passage 20'a and a position close to the outer end of the lead passage 20'a. Such a movement of the lead passage width regulating member 134 as described above can be controlled directly by the lengthwise moving member 31'a having the configuration similar to that of the lengthwise moving member 31a of the lead passage variable manipulation portion 31 for the pair of capturing members 32a, 32b shown in FIG. 3A. This is different from that the lead passage variable manipulation portion 31 shown in FIG. 3A includes the capturing member driving mechanism 31b in addition to the lead passage variable manipulation portion 31 in order to manipulate the pair of capturing members 32a, 32b.

Therefore, the blood vessel harvesting apparatus (harvester) 10 of the sixth embodiment, the configuration of the cutter main unit 12 of which is shown in FIGS. 12A and 12B, has more simple configuration in comparison with the blood vessel harvesting apparatus (harvester) 10 of the first embodiment, the configuration of the cutter main unit 12 of which is shown in FIGS. 3A to 3C, and the blood vessel harvesting apparatus (harvester) 10 of the second embodiment, the configuration of the cutter main unit 12 of which is shown in FIGS. 9A to 9D.

Figure 13A:
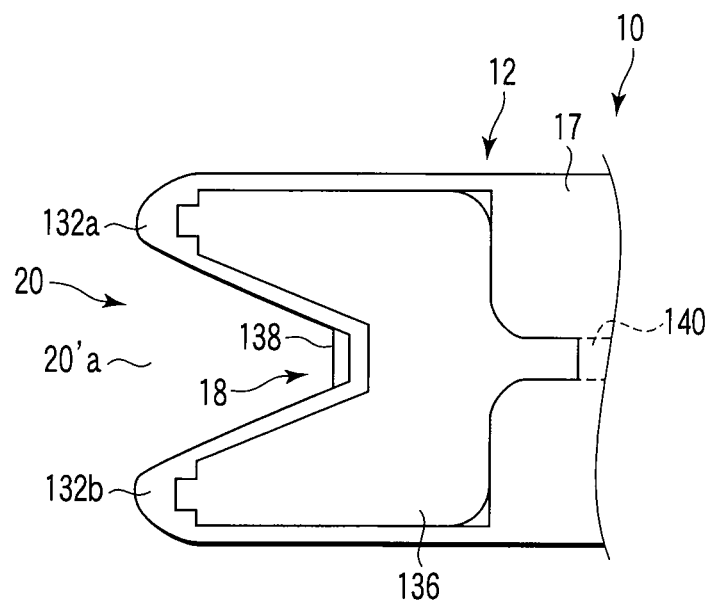
FIG. 13A is a schematic plan view showing a cutter main unit of a blood vessel harvesting apparatus (harvester) according to a sixth embodiment of the bipolar cutter of the present invention in a state in which a lead passage width regulating member is disposed at an inner end of a lead passage.

In this blood vessel harvesting apparatus (harvester) 10, when the lead passage variable manipulation slider 44 provided in the grip unit 16 shown in FIG. 1 is disposed at a position farthest away from the insertion unit 14 in the movable range of the lead passage variable manipulation slider 44 along the lengthwise center line of the insertion unit 14 on the grip unit 16, the lead passage width regulating member 134 connected to the lead passage variable manipulation slider 44 through the lengthwise moving member 31'a is disposed at a position closest to the inner end of the lead passage 20'a in the movable range of the lead passage width regulating member 134 (between the inner end of the lead passage 20'a and the position close to the outer end of the lead passage 20'a) along the lengthwise center line of the movable support body 17 in the front-end portion of the movable support body 17 as shown in FIG. 13A.

Figure 13B:
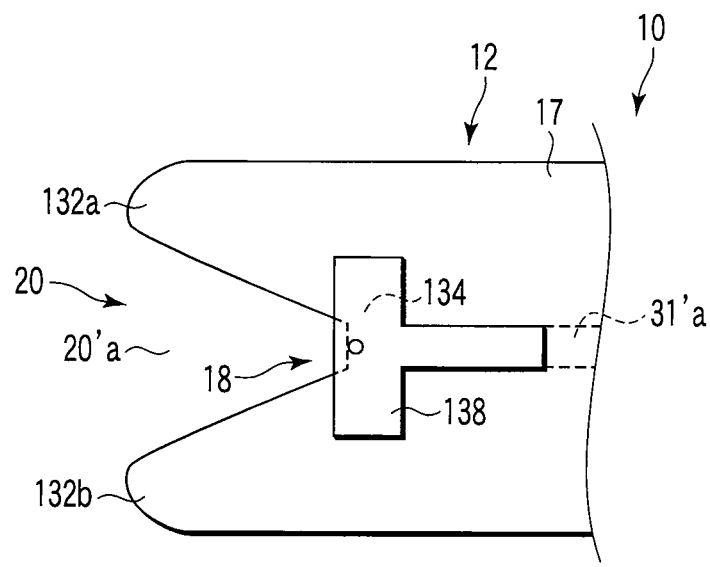
FIG. 13B is a schematic bottom view of the cutter main unit shown in FIG. 13A.

As a result, as shown in FIGS. 13A and 13B, the width at the inner end of the lead passage 20'a formed between the capturing members 132a, 132b of the guide portion 20 is regulated by the lead passage width regulating member 134 to become smallest.

In this blood vessel harvesting apparatus (harvester) 10, when the lead passage variable manipulation slider 44 provided in the grip unit 16 shown in FIG. 1 is disposed at a position closest to the insertion unit 14 in the movable range of the lead passage variable manipulation slider 44 along the lengthwise center line of the insertion unit 14 on the grip unit 16, the lead passage width regulating member 134 connected to the lead passage variable manipulation slider 44 through the lengthwise moving member 31'a is disposed at a position closest to the outer end of the lead passage 20'a in the movable range of the lead passage variable manipulation slider 44 (between the inner end of the lead passage 20'a and a position closer to the outer end of the lead passage 20'a than the inner end) along the lengthwise center line of the movable support body 17 in the front-end portion of the movable support body 17 as shown in FIG. 13C.

As a result, as shown in FIGS. 13C and 13D, the width at the inner end of the lead passage 20'a formed between the capturing members 132a, 132b of the guide portion 20 is regulated by the lead passage width regulating member 134 to become largest.

This means that, by disposing the lead passage variable manipulation slider 44 provided in the grip unit 16 shown in FIG. 1 in the blood vessel harvesting apparatus (harvester) 10 at any position in the movable range of the lead passage variable manipulation slider 44 along the lengthwise center line of the insertion unit 14 on the grip unit 16, the lead passage width regulating member 134 can be disposed at any position in the movable range along the lengthwise center line of the movable support body 17 in the lead passage 20'a between the capturing members 132a, 132b of the guide portion 20, and therefore the width at the inner end of the lead passage 20'a formed between the capturing members 132a, 132b can be set arbitrarily in the range between the smallest width shown in FIGS. 13A and 13B and the largest width shown in FIGS. 13C and 13D.

Further, the width at the inner end of the lead passage 20'a corresponding to the position of the lead passage variable manipulation slider 44 on the grip unit 16 can be recognized easily by the lead passage width index 46 disposed adjacent to the lead passage variable manipulation slider 44 on the outer surface of the grip unit 16.

In the blood vessel harvesting apparatus (harvester) 10 of the sixth embodiment, while the lead passage width regulating member 134 is disposed at the position closest to the inner end of the lead passage 20'a by the lead passage variable manipulation slider 44, the movable support body 17 of the insertion unit 14 is manipulated such that the branching end of the collateral vein 62a to be cut as shown in FIG. 5 is introduced into the lead passage 20'a. The branching end of the collateral vein 62a can be introduced into the lead passage 20'a until the outer circumferential surface of the introduced branching end of the collateral vein 62a contacts the facing edges regulating the lead passage 20'a in the pair of capturing members 132a, 132b (namely, until the outer circumferential surface of the introduced branching end of the collateral 62a contacts or extremely approaches the application electrode 136). Then, the lead passage width regulating member 134 is moved from the inner end toward the outer end of the lead passage 20'a by the lead passage variable manipulation slider 44 until the return electrode 138 at the front end of the lead passage width regulating member 134 contacts the introduced branching end of the collateral 62a.

Thus, since the width at the inner end of the lead passage 20'a can be set to the width corresponding to the diameter of the branching end of the collateral vein 62a introduced into the lead passage 20'a, the application electrode 136 along or adjacent to the pair of facing edges of the pair of capturing members 132a, 132b forming the lead passage 20'a therebetween and the return electrode 138 covering the front end (i.e., the inner end of the lead passage 20'a) of the front-end portion of the lead passage width regulating member 134 can be pressed surely against the branching end of the collateral vein 62a introduced into the inner end of the lead passage 20'a. As a result, the branching end of the collateral vein 62a introduced into the inner end of the lead passage 20'a can be cut by the high-frequency current passed from the application electrode 136 to the return electrode 138 and the cut surface can be cauterized (stop bleeding) in the bipolar cutting treatment portion 18 at the inner end of the lead passage 20'a.

Therefore, the blood vessel harvesting operation described with reference to FIGS. 4 to 7 can be performed quickly and the operated point in the patient body is early recovered after the operation.

[Modification of First Embodiment]

A modification of the first embodiment described above with reference to FIGS. 1 to 8D will be described with reference to FIGS. 14A and 14B.

Figure 14A:
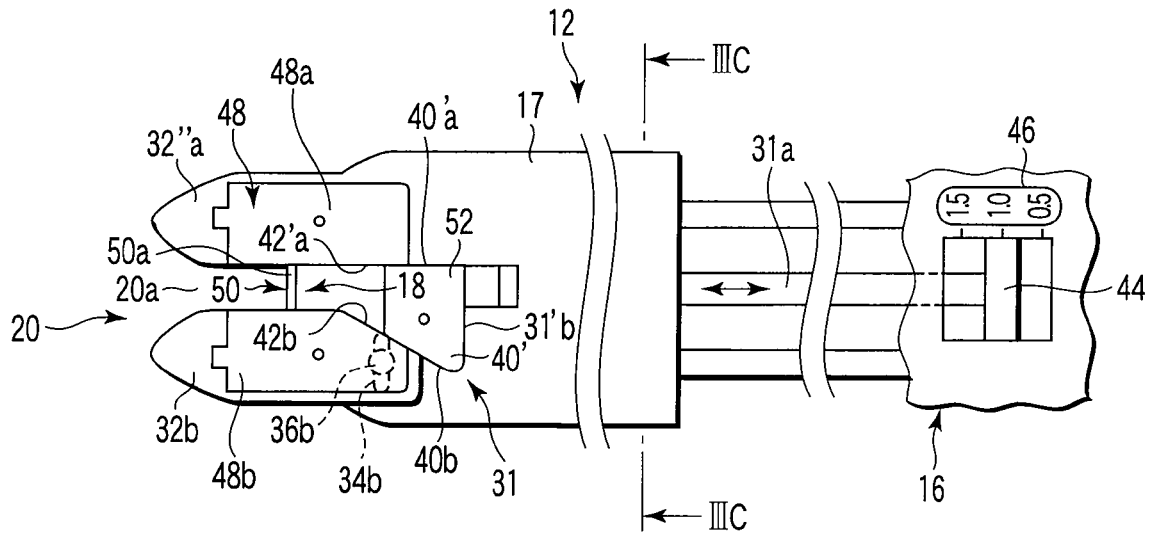
FIG. 14A is a schematic plan view of a modification of the cutter main unit of the blood vessel harvesting apparatus (harvester) shown in FIG. 3A.
Figure 14B:
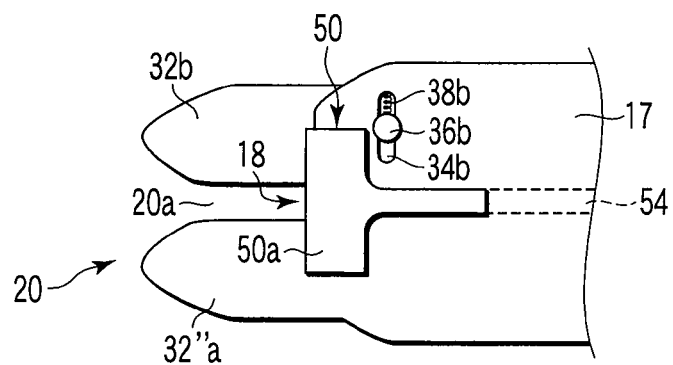
FIG. 14B is a bottom view of the modification of the cutter main unit shown in FIG. 14A.

FIG. 14A is a schematic plan view of a modification of the cutter main unit 12 of the blood vessel harvesting apparatus (harvester) 10 of the first embodiment shown in FIG. 3A, and FIG. 14B is a bottom view of the modification shown in FIG. 14A.

Most part of the structural elements of this modification is the same as those of the blood vessel harvesting apparatus (harvester) 10 of the first embodiment. Accordingly, in this modification, the same structural elements as those of the blood vessel harvesting apparatus (harvester) 10 of the first embodiment are designated by the same reference numerals designating the same structural elements of the blood vessel harvesting apparatus (harvester) 10 of the first embodiment corresponding thereto, and the detailed description thereof are omitted.

This modification differs from the blood vessel harvesting apparatus (harvester) 10 of the first embodiment in that, in the cutter main unit 12, one capturing member 32"a is integrally formed with the front-end portion of the movable support body 17 and cannot be moved to the front-end portion of the movable support body 17 while only the other capturing member 32b is provided in the front-end portion of the movable support body 17 to be movable to the front-end portion of the movable support body 17 and to vary the width of the lead passage 20a.

Therefore, in a cam member 40' of a capturing member driving mechanism 31'b, a cam surface 40'a corresponding to the one capturing member 32"a is in parallel to the moving direction of the cam member 40', and a cam sliding surface 42'a of the base-end portion of the one capturing member 32"a corresponding to the cam member 40' is also in parallel to the moving direction of the cam member 40'. As a result, in the movable range of the cam member 40' on the front-end portion of the movable support body 17, a part of the intermediate conductive terminal member 52 covering the cam surface 40'a of the cam member 40' is always electrically in contact with the conductive terminal member 48a covering the cam sliding surface 42'a on the base-end portion of the one capturing member 32"a.

In this modification, in the movable range of the cam member 40' in the front-end portion of the movable support body 17, with respect to the one capturing member 32"a formed integrally with the front-end portion of the movable support body 17, only the other capturing member 32b is moved in parallel to the one capturing member 32"a and to vary the width of the lead passage 20a, and the other capturing member 32b is moved in the direction intersecting the lengthwise center line of the front-end portion of the movable support body 17 (in this modification, the direction orthogonal to the lengthwise center line).

[Modification of Sixth Embodiment]

A modification of the sixth embodiment described above with reference to FIGS. 13A to 13D will be described with reference to FIGS. 15A and 15B.

FIG. 15A is a schematic plan view of a modification of the cutter main unit 12 of the blood vessel harvesting apparatus (harvester) 10 of the sixth embodiment shown in FIG. 13A, and FIG. 15B is a schematic bottom view of the modification shown in FIG. 15A.

Most part of the structural elements of this modification is the same as those of the blood vessel harvesting apparatus (harvester) 10 of the sixth embodiment. Accordingly, in this modification, the same structural elements as those of the blood vessel harvesting apparatus (harvester) 10 of the first embodiment are designated by the same reference numerals designating the same structural elements of the blood vessel harvesting apparatus (harvester) 10 of the first embodiment corresponding thereto, and the detailed description thereof are omitted.

This modification differs from the blood vessel harvesting apparatus (harvester) 10 of the sixth embodiment in that each of the pair of facing edges regulating the lead passage 20'a in the two capturing members 132'a, 132'b is formed in a step manner.

[Output Checking Device]

An example of an output checking device for the bipolar cutter of the invention will be described with reference to FIGS. 16 to 19.

The output checking device 150 of this example is used to check an output of the bipolar cutting treatment portion 18 provided in the front-end portion of the insertion unit 14 of each of the blood vessel harvesting apparatuses (harvesters) 10 according to the first to sixth embodiments and two modifications of the bipolar cutter of this invention shown in FIGS. 1 to 15D.

Particularly, as shown in FIGS. 16, 17A, and 17B, the output checking device 150 includes a placing member 152 to be placed on the outer surfaces of the pair of or three capturing members 32a and 32b, 32'a and 32'b, 82a, 82b, and 82c, 102a and 102b, 132a and 132b, 32"a and 32b, or 132'a and 132'b of the guide portion 20 of the front-end portion of the movable support body 17 provided in the front-end portion of the insertion unit 14 of the blood vessel harvesting apparatus (harvester) 10 according to each of the first to sixth embodiments and two modifications. The placing member 152 is made of an electrically-insulating material, and has a knob 154 in an outer surface facing in the opposite direction to the placing surface.

A rod-shaped insulating guide member 156 is integrally formed with the placing member 152 with the same material as the placing member 152 on the placing surface of the placing member 152. The insulating guide member 156 is extended in the direction intersecting the placing surface of the placing member 152. The insulating guide member 156 has a size with which the insulating guide member 156 can be inserted in the lead passage 20a, 84a, 84b, or 20'a of the guide portion 20 in the front-end portion of the insertion unit 14 of the blood vessel harvesting apparatus (harvester) 10 according to each of the first to sixth embodiments and two modifications.

An application electrode contacting member 158 is disposed on the placing surface of the placing member 152, and a return electrode contacting member 160 is supported on the extending end portion of the insulating guide member 156. A conductive line 162 extends in parallel with the insulating guide member 156 between the application electrode contacting member 158 and the return electrode contacting member 160, and both end portions of the conductive line 162 are electrically connected to the application electrode contacting member 158 and the return electrode contacting member 160 respectively.

A light emitting device 164 is further provided in the outer surface of the placing member 152, and the light emitting device 164 emits light when a predetermined high-frequency current is passed between the application electrode contacting member 158 and the return electrode contacting member 160 through the conductive line 162.

The insulating guide member 156 of the output checking device 150 is inserted to the inner end of the lead passage 20a, 84a, 84b, or 20'a of the guide portion 20 in the front-end portion of the movable support body 17 provided in the front-end portion of the insertion unit 14 of each of the blood vessel harvesting apparatuses (harvesters) 10 according to the first to sixth embodiments and two modifications, and the placing member 152 thereof is placed on the outer surfaces of the pair of or three capturing members 32a and 32b, 32'a and 32'b, 82a, 82b, and 82c, 102a and 102b, 132a and 132b, 32"a and 32b, or 132'a and 132'b of the guide portion 20 of the front-end portion of the movable support body 17 provided in the front-end portion of the insertion unit 14 of each of the blood vessel harvesting apparatuses (harvesters) 10 according to the first to sixth embodiments and two modifications.

Accordingly, the return electrode contacting member 160 of the extended end portion of the insulating guide member 156 in the output checking device 150 is electrically connected to the return electrode 50, 88, 112, or 138 at the inner end of the lead passage 20a, 84a, 84b, or 20'a of the guide portion 20 of the front-end portion of the movable support body 17 provided in the front-end portion of the insertion unit 14 of the blood vessel harvesting apparatus (harvester) 10 according to each of the first to sixth embodiments and two modifications. At the same time, the application electrode contacting member 158 in the placing surface of the placing member 152 is electrically connected to the application electrode 48, 86, 110, or 136 of the guide portion 20 of the front-end portion of the movable support body 17 provided in the front-end portion of the insertion unit 14 of the blood vessel harvesting apparatus (harvester) 10 according to each of the first to sixth embodiments and two modifications.

Figure 18:
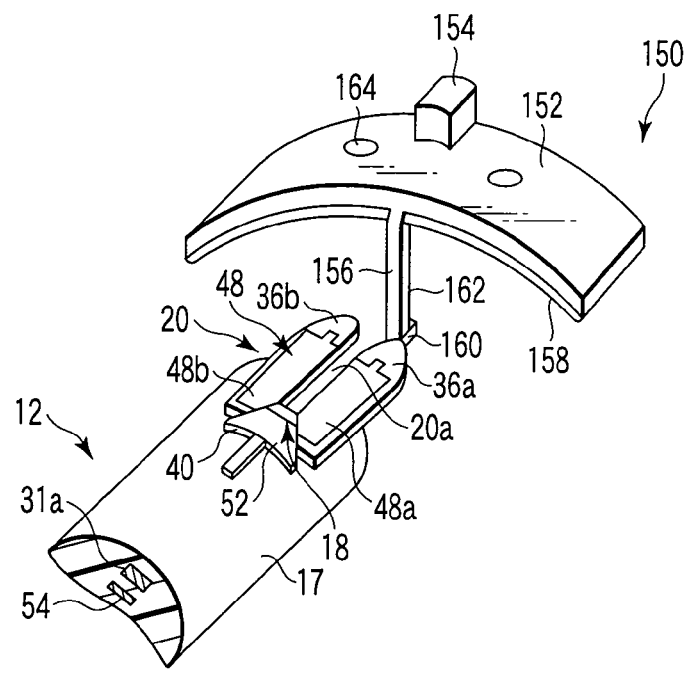
FIG. 18 is a perspective view schematically showing a state in which the output checking device shown in FIG. 16 is used to check an output of the bipolar cutter of the present invention.

FIG. 18 schematically shows a state just before the insulating guide member 156 of the output checking device 150 is inserted to the inner end of the lead passage 20a of the guide portion 20 in the front-end portion of the movable support body 17 provided in the front-end portion of the insertion unit 14 of the blood vessel harvesting apparatus (harvester) 10 according to the first embodiment while the placing member 152 is placed on the outer surfaces of the pair of capturing members 32a, 32b of the guide portion 20 of the front-end portion of the movable support body 17 provided in the front-end portion of the insertion unit 14 of the blood vessel harvesting apparatus (harvester) 10 according to the first embodiment.

Figure 19:
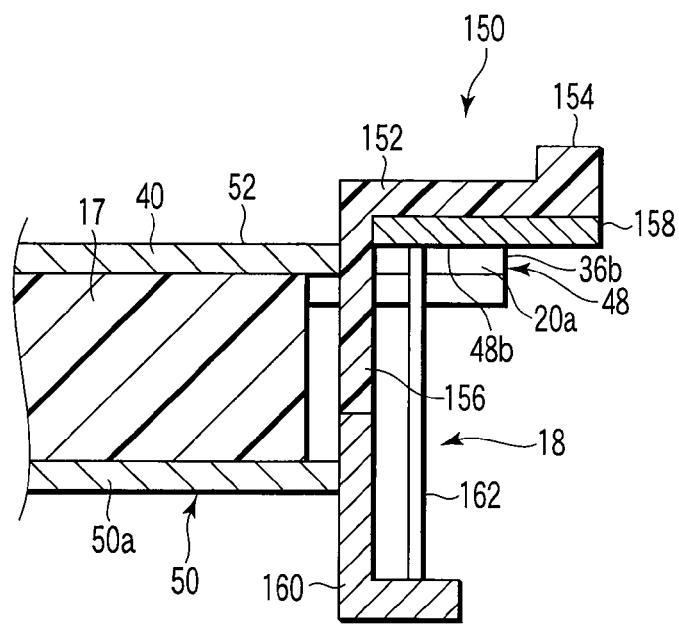
FIG. 19 is a longitudinal sectional view schematically showing a state in which the output checking device shown in FIG. 16 is used to check the output of the bipolar cutter of the present invention.

FIG. 19 schematically shows a state in which the return electrode contacting member 160 of the extending end portion of the insulating guide member 156 of the output checking device 150 is electrically connected to the return electrode 50 at the inner end of the lead passage 20a of the guide portion 20 of the front-end portion of the movable support body 17 provided in the front-end portion of the insertion unit 14 of the blood vessel harvesting apparatus (harvester) 10 according to the first embodiment while the application electrode contacting member 158 on the placing surface of the placing member 152 is electrically connected to the application electrode 48 of the guide portion 20 of the front-end portion of the movable support body 17 provided in the front-end portion of the insertion unit 14 of the blood vessel harvesting apparatus (harvester) 10 according to the first embodiment.

Before the insertion unit 14 of each of the blood vessel harvesting apparatuses (harvesters) 10 according to each of the first to sixth embodiments and two modifications is inserted in the body of the living thing, the high-frequency current from the high-frequency power supply S shown in FIG. 1 is supplied to the application electrode 48, 86, 110, or 136 of the guide portion 20 of the front-end portion of the movable support body 17 provided in the front-end portion of the insertion unit 14 of each of the blood vessel harvesting apparatuses (harvesters) 10 according to the first to sixth embodiments and two modifications. At this time, when the predetermined high-frequency current is passed from the application electrode 48, 86, 110, or 136 to the corresponding return electrode 50, 88, 112, or 138 through the application electrode contacting member 158, conductive line 162, and return electrode contacting member 160 of the output checking device 150 and the light emitting device 164 on the outer surface of the placing member 152 emits light, it can be confirmed that the bipolar cutting treatment portion 18 of each of the blood vessel harvesting apparatuses (harvesters) 10 according to the first to sixth embodiments and two modifications is normally operated. When the light emitting device 164 does not emit light, it can be confirmed that the bipolar cutting treatment portion 18 of each of the blood vessel harvesting apparatuses (harvesters) 10 according to each of the first to sixth embodiments and two modifications has broken down.

By using the output checking device 150 in such a manner as described above, it can confirm easily whether the bipolar cutting treatment portion 18 of each of the blood vessel harvesting apparatuses (harvesters) 10 according to the first to sixth embodiments and two modifications is normally operated or has broken down.

Instead of using the light emitting device 164, the conductive line 162 can be configured to emit light or be fused when a predetermined high-frequency current is passed between the application electrode contacting member 158 and the return electrode contacting member 160 through the conductive line 162.

According to the concept of the invention, the bipolar cutter of this invention can be used solely without the endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A bipolar cutter for cutting a living tissue, comprising:
an insertion unit which has a first base-end portion, a first front-end portion and a lengthwise axis extending from the first base-end portion to the first front-end portion, and which is adapted to be inserted in the living tissue;
a support body having a second base-end portion and a second front-end portion, for being movable in a back and forth direction to be projectable from the first front-end portion of the insertion unit;
a manipulation part mounted in the second base-end portion, configured for manipulating the support body to be movable in a back and forth direction along the lengthwise axis and to be projectable from the first front-end portion of the insertion unit;
a pair of capturing members, having a third front-end portion and a third base-end portion mounted on the second front-end portion, configured for capturing the living tissue, extending from the third front-end portion to the third base-end portion, being movable in a direction perpendicular to the lengthwise axis, and being arranged along the lengthwise axis in parallel thereto, the paired capturing members having projecting ends at the third front-end portion to lead the living tissue along the lengthwise axis, the paired capturing members forming a lead passage for leading the living tissue between the paired capturing members from the projecting ends toward the third base-end portion, and the width between the projecting ends of the paired capturing members being wider than the width between the paired capturing members excluding the projecting ends;
a variable manipulation part being able to manipulate the paired capturing members to open and close relative to each other in a direction crossing a lengthwise axis of the support body at a right angle, for leading the living tissue in the lead passage from the third front-end portion to the third base-end portion, and being able to vary the lead passage between the paired capturing members by a predetermined width;
an application electrode configured for applying electric current on the living tissue, and provided on at least one of the paired capturing members, and
a return electrode fixed at the second front-end portion of the support body between the paired capturing members and receiving electric energy from the application electrode.

2. The bipolar cutter according to claim 1,
wherein the variable manipulation part includes:
a moving member which is movable along the lengthwise axis of the support body; and
a driving mechanism which moves the capturing members in the direction crossing the lengthwise axis of the support body at a right angle in accordance with the movement of the moving member.

3. The bipolar cutter according to claim 2, wherein are urged to approach each other in the direction crossing the lengthwise axis of the support body at a right angle,
the driving mechanism includes a cam member interposed between the moving member and the capturing members, and
the cam member includes cam surfaces which contact the capturing members and which move the urged capturing members in the direction crossing lengthwise axis of the support body at a right angle, in accordance with the movement of the moving member.

4. The bipolar cutter according to claim 2, wherein the pair of capturing members is rotationally provided in the first front-end portion of the insertion unit, and
the capturing member driving mechanism includes a link mechanism which is interposed between the moving member and the pair of capturing members and which rotates the pair of capturing members in accordance with the movement of the moving member.

5. The bipolar cutter according to claim 4, wherein the pair of capturing members is urged in a direction in which the width of the lead passage is decreased.

6. The bipolar cutter according to claim 1, wherein the paired capturing members include facing edges which form the lead passage between them when the capturing members are positioned in an open position.

7. The bipolar cutter according to claim 6, wherein the capturing members have outer side edges which are located outward from the facing edges in the direction crossing the lengthwise axis of the support body at a right angle, and the outer side edges of the capturing members are located within a size of the support body in the direction crossing the lengthwise axis of the support body at a right angle while the capturing members are moved in the direction crossing the lengthwise axis of the support body at a right angle.

8. The bipolar cutter according to claim 1, wherein the variable manipulation part has a fourth front-end portion toward the third front-end portion and a fourth-base end portion extending to the first base-end portion of the insertion unit, and wherein when the variable manipulation part is moved along the lengthwise axis of the support body toward the third front-end portion, the paired capturing members are opened to form the lead passage between them and the return electrode is exposed in the lead passage between the paired and opened capturing members.

9. The bipolar cutter according to claim 1, wherein the variable manipulation part includes a spring-like urging member provided in the direction perpendicular to the lengthwise axis of the support body, for urging the paired capturing members to approach the lengthwise axis of the support body and to set a width of the lead passage to correspond to a size of the living tissue.

* * * * *